United States Patent
Von Arx et al.

(10) Patent No.: US 8,046,080 B2
(45) Date of Patent: *Oct. 25, 2011

(54) TELEMETRY DUTY CYCLE MANAGEMENT SYSTEM FOR AN IMPLANTABLE MEDICAL DEVICE

(75) Inventors: Jeffrey A. Von Arx, Minneapolis, MN (US); Ron Balczewski, Bloomington, MN (US); Scott T. Mazar, Woodbury, MN (US); William J. Linder, Golden Valley, MN (US); William R. Mass, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/713,669

(22) Filed: Feb. 26, 2010

(65) Prior Publication Data

US 2010/0152816 A1    Jun. 17, 2010

Related U.S. Application Data

(63) Continuation of application No. 11/325,584, filed on Jan. 4, 2006, now Pat. No. 7,738,964, which is a continuation of application No. 10/025,223, filed on Dec. 19, 2001, now Pat. No. 6,993,393.

(51) Int. Cl.
*A61N 1/00*    (2006.01)
(52) U.S. Cl. ..................................... 607/60
(58) Field of Classification Search ............... 607/60
See application file for complete search history.

(56) References Cited

U.S. PATENT DOCUMENTS

| | | |
|---|---|---|
| 3,914,586 A | 10/1975 | McIntosh |
| 4,341,982 A | 7/1982 | Lahti et al. |
| 4,404,972 A | 9/1983 | Gordon et al. |
| 4,441,498 A | 4/1984 | Nordling |
| 4,486,739 A | 12/1984 | Franaszek et al. |
| 4,539,992 A | 9/1985 | Calfee et al. |
| 4,542,535 A | 9/1985 | Bates et al. |
| 4,543,954 A | 10/1985 | Cook et al. |
| 4,561,443 A | 12/1985 | Hogrefe et al. |

(Continued)

FOREIGN PATENT DOCUMENTS

EP    0607638 A2    7/1994

(Continued)

OTHER PUBLICATIONS

"U.S. Appl. No. 10/025,183, Notice of Allowance mailed Sep. 28, 2009", 5 pgs.
"U.S. Appl. No. 10/025,183, Appeal Brief filed Dec. 29, 2005", 27 pgs.
"U.S. Appl. No. 10/025,183, Final Office Action mailed Jan. 13, 2005", 7 pgs.
"U.S. Appl. No. 10/025,183, Final Office Action mailed May 25, 2005", 9 pgs.
"U.S. Appl. No. 10/025,183, Final Office Action mailed Jul. 31, 2006", 7 pgs.
"U.S. Appl. No. 10/025,183, Final Office Action mailed Aug. 3, 2004", 7 pgs.
"U.S. Appl. No. 10/025,183, Non-Final Office Action mailed Feb. 15, 2006", 5 pgs.
"U.S. Appl. No. 10/025,183, Non-Final Office Action mailed Feb. 19, 2009", 5 pgs.

(Continued)

*Primary Examiner* — George Manuel
(74) *Attorney, Agent, or Firm* — Schwegman, Lundberg & Woessner, P.A.

(57) ABSTRACT

An implantable medical device comprising a far field RF transmitter and receiver, a controller circuit communicatively coupled to the RF transmitter and receiver, and a wakeup timer circuit integral to, or communicatively coupled to, the controller. The controller is configured to initiate power up of the RF transmitter and receiver during a wakeup interval defined by the wakeup timer circuit, detect a digital key received from a second device during the wakeup interval, transmit a response using the RF transmitter when the digital key is received, and receive a communication from the second device and resynchronize the wake-up timer according to a time of the communication.

20 Claims, 6 Drawing Sheets

U.S. PATENT DOCUMENTS

| | | | |
|---|---|---|---|
| 4,562,841 A | 1/1986 | Brockway et al. | |
| 4,613,937 A | 9/1986 | Batty, Jr. | |
| 4,731,814 A | 3/1988 | Becker et al. | |
| 4,803,987 A | 2/1989 | Calfee et al. | |
| 4,944,299 A | 7/1990 | Silvian | |
| 4,945,909 A | 8/1990 | Fearnot et al. | |
| 4,987,897 A | 1/1991 | Funke | |
| 5,025,808 A | 6/1991 | Hafner | |
| 5,074,308 A | 12/1991 | Sholder et al. | |
| 5,080,096 A | 1/1992 | Hooper et al. | |
| 5,109,853 A | 5/1992 | Taicher et al. | |
| 5,113,869 A | 5/1992 | Nappholz et al. | |
| 5,171,977 A | 12/1992 | Morrison | |
| 5,230,003 A | 7/1993 | Dent et al. | |
| 5,287,384 A | 2/1994 | Avery et al. | |
| 5,292,343 A | 3/1994 | Blanchette et al. | |
| 5,300,093 A | 4/1994 | Koestner et al. | |
| 5,342,408 A | 8/1994 | deCoriolis et al. | |
| 5,350,411 A | 9/1994 | Ryan et al. | |
| 5,350,412 A | 9/1994 | Hoegnelid et al. | |
| 5,370,666 A | 12/1994 | Lindberg et al. | |
| 5,404,877 A | 4/1995 | Nolan et al. | |
| 5,466,246 A | 11/1995 | Silvian | |
| 5,476,488 A | 12/1995 | Morgan et al. | |
| 5,516,285 A | 5/1996 | Yacker et al. | |
| 5,532,708 A | 7/1996 | Krenz et al. | |
| 5,562,713 A | 10/1996 | Silvian | |
| 5,568,510 A | 10/1996 | Tam | |
| 5,577,087 A | 11/1996 | Furuya | |
| 5,593,430 A | 1/1997 | Renger | |
| 5,603,331 A | 2/1997 | Heemels et al. | |
| 5,630,835 A | 5/1997 | Brownlee | |
| 5,650,759 A | 7/1997 | Hittman et al. | |
| 5,683,432 A | 11/1997 | Goedeke et al. | |
| 5,694,952 A | 12/1997 | Lidman et al. | |
| 5,697,958 A | 12/1997 | Paul et al. | |
| 5,725,559 A | 3/1998 | Alt et al. | |
| 5,733,313 A | 3/1998 | Barreras, Sr. et al. | |
| 5,737,419 A | 4/1998 | Ganesan | |
| 5,752,976 A | 5/1998 | Duffin et al. | |
| 5,752,977 A | 5/1998 | Grevious et al. | |
| 5,759,199 A | 6/1998 | Snell et al. | |
| 5,764,699 A | 6/1998 | Needham et al. | |
| 5,766,232 A | 6/1998 | Grevious et al. | |
| 5,807,397 A | 9/1998 | Barreras | |
| 5,833,603 A | 11/1998 | Kovacs et al. | |
| 5,843,139 A | 12/1998 | Goedeke et al. | |
| 5,861,019 A | 1/1999 | Sun et al. | |
| 5,881,101 A | 3/1999 | Furman et al. | |
| 5,895,485 A | 4/1999 | Loechel et al. | |
| 5,898,397 A | 4/1999 | Murray | |
| 5,904,708 A | 5/1999 | Goedeke | |
| 5,940,384 A | 8/1999 | Carney et al. | |
| 6,009,350 A | 12/1999 | Renken | |
| 6,028,527 A | 2/2000 | Soenen et al. | |
| 6,044,485 A | 3/2000 | Dent et al. | |
| 6,083,248 A | 7/2000 | Thompson | |
| 6,093,146 A | 7/2000 | Filangeri | |
| 6,115,634 A | 9/2000 | Donders et al. | |
| 6,115,636 A | 9/2000 | Ryan | |
| 6,155,208 A | 12/2000 | Schell et al. | |
| 6,167,310 A | 12/2000 | Grevious | |
| 6,167,312 A | 12/2000 | Goedeke | |
| 6,169,925 B1 | 1/2001 | Villaseca et al. | |
| 6,200,265 B1 | 3/2001 | Walsh et al. | |
| 6,223,083 B1 | 4/2001 | Rosar | |
| 6,240,317 B1 | 5/2001 | Villaseca et al. | |
| 6,249,700 B1 | 6/2001 | Alt | |
| 6,263,246 B1 | 7/2001 | Goedeke et al. | |
| 6,275,737 B1 | 8/2001 | Mann | |
| 6,309,350 B1 | 10/2001 | VanTassel et al. | |
| 6,329,920 B1 | 12/2001 | Morrison et al. | |
| 6,336,900 B1 | 1/2002 | Alleckson et al. | |
| 6,336,903 B1 | 1/2002 | Bardy | |
| 6,385,318 B1 | 5/2002 | Oishi | |
| 6,388,628 B1 | 5/2002 | Dettloff et al. | |
| 6,416,471 B1 | 7/2002 | Kumar et al. | |
| 6,424,867 B1 | 7/2002 | Snell et al. | |
| 6,427,088 B1 | 7/2002 | Bowman, IV et al. | |
| 6,434,429 B1 | 8/2002 | Kraus et al. | |
| 6,443,891 B1 * | 9/2002 | Grevious | 600/302 |
| 6,456,256 B1 | 9/2002 | Amundson et al. | |
| 6,463,329 B1 | 10/2002 | Goedeke | |
| 6,470,215 B1 | 10/2002 | Kraus et al. | |
| 6,482,154 B1 | 11/2002 | Haubrich et al. | |
| 6,490,487 B1 | 12/2002 | Kraus et al. | |
| 6,505,072 B1 | 1/2003 | Linder et al. | |
| 6,527,729 B1 | 3/2003 | Turcott | |
| 6,531,982 B1 | 3/2003 | White et al. | |
| 6,535,766 B1 | 3/2003 | Thompson et al. | |
| 6,562,000 B2 | 5/2003 | Thompson et al. | |
| 6,562,001 B2 | 5/2003 | Lebel et al. | |
| 6,564,104 B2 | 5/2003 | Nelson et al. | |
| 6,564,105 B2 | 5/2003 | Starkweather et al. | |
| 6,574,509 B1 | 6/2003 | Kraus et al. | |
| 6,574,510 B2 | 6/2003 | Von Arx et al. | |
| 6,577,900 B1 | 6/2003 | Silvian | |
| 6,577,901 B2 | 6/2003 | Thompson et al. | |
| 6,582,365 B1 | 6/2003 | Hines et al. | |
| 6,585,644 B2 | 7/2003 | Lebel et al. | |
| 6,600,949 B1 | 7/2003 | Turcott | |
| 6,600,952 B1 | 7/2003 | Snell et al. | |
| 6,602,191 B2 | 8/2003 | Quy | |
| 6,609,029 B1 | 8/2003 | Mann et al. | |
| 6,614,406 B2 | 9/2003 | Amundson et al. | |
| 6,622,043 B1 | 9/2003 | Kraus et al. | |
| 6,622,050 B2 | 9/2003 | Thompson | |
| 6,624,786 B2 | 9/2003 | Boyle | |
| 6,648,821 B2 | 11/2003 | Lebel et al. | |
| 6,659,948 B2 | 12/2003 | Lebel et al. | |
| 6,662,048 B2 | 12/2003 | Balczewski et al. | |
| 6,671,328 B1 | 12/2003 | Poon et al. | |
| 6,675,045 B2 | 1/2004 | Mass et al. | |
| 6,687,546 B2 | 2/2004 | Lebel et al. | |
| 6,708,065 B2 | 3/2004 | Von Arx et al. | |
| 6,716,165 B1 | 4/2004 | Flanders et al. | |
| 6,741,886 B2 | 5/2004 | Yonce | |
| 6,763,269 B2 | 7/2004 | Cox | |
| 6,768,730 B1 | 7/2004 | Whitehill | |
| 6,801,807 B2 | 10/2004 | Abrahamson | |
| 6,804,559 B1 | 10/2004 | Kraus et al. | |
| 6,809,701 B2 | 10/2004 | Amundson et al. | |
| 6,844,854 B2 | 1/2005 | Johnson et al. | |
| 6,868,288 B2 | 3/2005 | Thompson | |
| 6,889,081 B2 | 5/2005 | Hsu | |
| 6,907,291 B1 | 6/2005 | Snell et al. | |
| 6,970,735 B2 | 11/2005 | Uber, III et al. | |
| 6,978,181 B1 | 12/2005 | Snell | |
| 6,985,088 B2 | 1/2006 | Goetz et al. | |
| 6,985,773 B2 | 1/2006 | Von Arx et al. | |
| 6,993,393 B2 | 1/2006 | Von Arx et al. | |
| 7,013,178 B2 | 3/2006 | Reinke et al. | |
| 7,027,872 B2 | 4/2006 | Thompson | |
| 7,047,076 B1 | 5/2006 | Li et al. | |
| 7,069,086 B2 | 6/2006 | Von Arx | |
| 7,107,085 B2 | 9/2006 | Doi | |
| 7,110,823 B2 | 9/2006 | Whitehurst et al. | |
| 7,155,290 B2 | 12/2006 | Von Arx et al. | |
| 7,218,969 B2 | 5/2007 | Vallapureddy et al. | |
| 7,228,182 B2 | 6/2007 | Healy et al. | |
| 7,274,642 B2 | 9/2007 | Sako et al. | |
| 7,319,903 B2 | 1/2008 | Bange et al. | |
| 7,324,012 B2 | 1/2008 | Mann et al. | |
| 7,359,753 B2 | 4/2008 | Bange et al. | |
| 7,406,349 B2 | 7/2008 | Seeberger et al. | |
| 7,519,430 B2 | 4/2009 | Von Arx et al. | |
| 7,539,541 B2 | 5/2009 | Quiles et al. | |
| 7,573,422 B2 | 8/2009 | Harvey et al. | |
| 7,610,065 B2 | 10/2009 | Vallapureddy et al. | |
| 7,664,553 B2 | 2/2010 | Roberts | |
| 7,668,596 B2 | 2/2010 | Von Arx et al. | |
| 7,729,776 B2 | 6/2010 | Von Arx et al. | |
| 7,738,964 B2 | 6/2010 | Von Arx et al. | |
| 7,860,574 B2 | 12/2010 | Von Arx et al. | |
| 7,881,802 B2 | 2/2011 | Quiles et al. | |
| 2001/0019614 A1 | 9/2001 | Madoukh | |
| 2001/0027331 A1 | 10/2001 | Thompson | |

| | | | |
|---|---|---|---|
| 2001/0047125 A1 | 11/2001 | Quy | |
| 2002/0013614 A1 | 1/2002 | Thompson | |
| 2002/0019606 A1 | 2/2002 | Lebel et al. | |
| 2002/0046276 A1 | 4/2002 | Coffey et al. | |
| 2002/0049480 A1 | 4/2002 | Lebel et al. | |
| 2002/0062139 A1 | 5/2002 | Ding | |
| 2002/0065509 A1 | 5/2002 | Lebel et al. | |
| 2002/0065539 A1 | 5/2002 | Von Arx et al. | |
| 2002/0065540 A1 | 5/2002 | Lebel et al. | |
| 2002/0109621 A1 | 8/2002 | Khair et al. | |
| 2002/0115912 A1 | 8/2002 | Muraki et al. | |
| 2002/0120838 A1 | 8/2002 | Abdulkader | |
| 2002/0143372 A1 | 10/2002 | Snell et al. | |
| 2002/0147388 A1 | 10/2002 | Mass et al. | |
| 2002/0159545 A1 | 10/2002 | Ramesh et al. | |
| 2002/0173830 A1 | 11/2002 | Starkweather et al. | |
| 2003/0018369 A1 | 1/2003 | Thompson et al. | |
| 2003/0028902 A1 | 2/2003 | Cubley et al. | |
| 2003/0041866 A1 | 3/2003 | Linberg et al. | |
| 2003/0050535 A1 | 3/2003 | Bowman, IV et al. | |
| 2003/0065919 A1 | 4/2003 | Albert et al. | |
| 2003/0074036 A1 | 4/2003 | Prutchi et al. | |
| 2003/0083719 A1 | 5/2003 | Shankar et al. | |
| 2003/0114897 A1 | 6/2003 | Von Arx et al. | |
| 2003/0114898 A1 | 6/2003 | Von Arx et al. | |
| 2003/0135246 A1 | 7/2003 | Mass et al. | |
| 2003/0146835 A1 | 8/2003 | Carter | |
| 2003/0149459 A1 | 8/2003 | Von Arx et al. | |
| 2003/0159048 A1 | 8/2003 | Matsumoto et al. | |
| 2003/0174069 A1 | 9/2003 | Goetz et al. | |
| 2003/0216793 A1 | 11/2003 | Karlsson et al. | |
| 2004/0009815 A1 | 1/2004 | Zotto et al. | |
| 2004/0030260 A1 | 2/2004 | Von Arx | |
| 2004/0047434 A1 | 3/2004 | Waltho | |
| 2004/0102815 A1 | 5/2004 | Balczewski et al. | |
| 2004/0106967 A1 | 6/2004 | Von Arx et al. | |
| 2004/0122489 A1 | 6/2004 | Mazar et al. | |
| 2004/0167587 A1 | 8/2004 | Thompson | |
| 2004/0168071 A1 | 8/2004 | Silverbrook | |
| 2004/0247047 A1 | 12/2004 | Dennis et al. | |
| 2004/0260363 A1 | 12/2004 | Von Arx et al. | |
| 2004/0263273 A1 | 12/2004 | Ahmed | |
| 2005/0203582 A1 | 9/2005 | Healy et al. | |
| 2005/0204134 A1 | 9/2005 | Von Arx et al. | |
| 2005/0222933 A1 | 10/2005 | Wesby | |
| 2005/0240245 A1 | 10/2005 | Bange et al. | |
| 2005/0283208 A1 | 12/2005 | Von Arx et al. | |
| 2005/0288738 A1 | 12/2005 | Bange et al. | |
| 2006/0025834 A1 | 2/2006 | Von Arx et al. | |
| 2006/0029100 A1 | 2/2006 | Dove | |
| 2006/0030901 A1 | 2/2006 | Quiles et al. | |
| 2006/0030902 A1 | 2/2006 | Quiles et al. | |
| 2006/0030903 A1 | 2/2006 | Seeberger et al. | |
| 2006/0030904 A1 | 2/2006 | Quiles | |
| 2006/0071756 A1 | 4/2006 | Steeves | |
| 2006/0116744 A1 | 6/2006 | Von Arx et al. | |
| 2006/0194615 A1 | 8/2006 | Vallapureddy et al. | |
| 2007/0118188 A1 | 5/2007 | Von Arx et al. | |
| 2007/0260293 A1 | 11/2007 | Carpenter et al. | |
| 2007/0282398 A1 | 12/2007 | Healy et al. | |
| 2008/0114412 A1 | 5/2008 | Bange et al. | |
| 2010/0106224 A1 | 4/2010 | Von Arx et al. | |
| 2010/0114233 A1 | 5/2010 | Von Arx et al. | |
| 2011/0066211 A1 | 3/2011 | Von Arx et al. | |

FOREIGN PATENT DOCUMENTS

| | | |
|---|---|---|
| EP | 1050265 A2 | 11/2000 |
| EP | 1062985 A2 | 12/2000 |
| EP | 1308184 A2 | 5/2003 |
| EP | 1495783 A1 | 1/2005 |
| WO | WO-9500202 A1 | 1/1995 |
| WO | WO-9819400 A1 | 5/1998 |
| WO | WO-9912302 A1 | 3/1999 |
| WO | WO-03053515 A1 | 7/2003 |
| WO | WO-2005099816 A1 | 10/2005 |
| WO | WO-2005099817 A1 | 10/2005 |

OTHER PUBLICATIONS

"U.S. Appl. No. 10/025,183, Non-Final Office Action mailed Mar. 4, 2004", 5 pgs.

"U.S. Appl. No. 10/025,183, Non-Final Office Action mailed Mar. 26, 2007", 4 pgs.

"U.S. Appl. No. 10/025,183, Non-Final Office Action mailed Dec. 10, 2007", 4 pgs.

"U.S. Appl. No. 10/025,183, Notice of Allowance mailed Sep. 14, 2007", 4 pgs.

"U.S. Appl. No. 10/025,183, Notice of Allowance mailed Sep. 18, 2008", 7 pgs.

"U.S. Appl. No. 10/025,183, Response filed Jan. 31, 2007 to Final Office Action mailed Jul. 31, 2006", 11 pgs.

"U.S. Appl. No. 10/025,183, Response filed Apr. 13, 2005 to Final Office Action mailed Jan. 13, 2005", 11 pgs.

"U.S. Appl. No. 10/025,183, Response filed May 12, 2008 to Non-Final Office Action mailed Dec. 10, 2007", 10 pgs.

"U.S. Appl. No. 10/025,183, Response filed May 15, 2006 to Non-Final Office Action mailed Feb. 15, 2006", 11 pgs.

"U.S. Appl. No. 10/025,183, Response filed Jun. 2, 2004 to Non-Final Office Action mailed Mar. 4, 2004", 11 pgs.

"U.S. Appl. No. 10/025,183, Response filed Jun. 12, 2009 to Non Final Office Action mailed Feb. 19, 2009", 10 pgs.

"U.S. Appl. No. 10/025,183, Response filed Jun. 26, 2007 to Non-Final Office Action mailed Mar. 26, 2007", 14 pgs.

"U.S. Appl. No. 10/025,183, Response filed Dec. 3, 2004 to Final Office Action mailed Aug. 3, 2004", 11 pgs.

"U.S. Appl. No. 10/025,223, Communication filed Nov. 16, 2004 to Final Office Action mailed Aug. 16, 2004", 1 pg.

"U.S. Appl. No. 10/025,223, Final Office Action mailed Aug. 16, 2004", 9 pgs.

"U.S. Appl. No. 10/025,223, Final Office Action mailed Aug. 16, 2004", 7 pgs.

"U.S. Appl. No. 10/025,223, Final Office Action mailed Sep. 10, 2004", 7 pgs.

"U.S. Appl. No. 10/025,223, Final Office Action mailed Sep. 10, 2004", 7 pgs.

"U.S. Appl. No. 10/025,223, Non Final Office Action mailed Mar. 1, 2005", 8 pgs.

"U.S. Appl. No. 10/025,223, Non Final Office Action mailed Mar. 19, 2004", 6 pgs.

"U.S. Appl. No. 10/025,223, Non-Final Office Action mailed Mar. 19, 2004", 4 pgs.

"U.S. Appl. No. 10/025,223, Non-Final Office Action mailed Mar. 1, 2005", 6 pgs.

"U.S. Appl. No. 10/025,223, Notice of Allowance mailed Aug. 10, 2005", 6 pgs.

"U.S. Appl. No. 10/025,223, Notice of Allowance mailed Aug. 10, 2005", 4 pgs.

"U.S. Appl. No. 10/025,223, Response filed Jan. 10, 2005 to Final Office Action mailed Sep. 10, 2004", 10 pgs.

"U.S. Appl. No. 10/025,223, Response filed Jun. 21, 2004 to Non Final Office Action mailed Mar. 19, 2004", 9 pgs.

"U.S. Appl. No. 10/025,223, Response filed Jun. 30, 2005 to Non Final Office Action mailed Mar. 1, 2005", 10 pgs.

"U.S. Appl. No. 10/071,255, Non Final Office Action mailed Jan. 7, 2005", 6 pgs.

"U.S. Appl. No. 10/071,255, Notice of allowance mailed Jun. 15, 2005", 4 pgs.

"U.S. Appl. No. 10/071,255, Preliminary Amendment filed Oct. 5, 2005", 12 pgs.

"U.S. Appl. No. 10/071,255, Response and Preliminary Amendment filed Oct. 20, 2004 to Restriction Requirement mailed Sep. 28, 2004", 7 pgs.

"U.S. Appl. No. 10/071,255, Response and Preliminary Amendment filed Oct. 20, 2004 to Restriction Requirement mailed Sep. 28, 2004", 10 pgs.

"U.S. Appl. No. 10/071,255, Response filed Apr. 7, 2005 non-final office action mailed Jan. 7, 2005", 12 pgs.

"U.S. Appl. No. 10/071,255, Restriction Requirement mailed Sep. 28, 2004", 5 pgs.

"U.S. Appl. No. 10/269,905, Non Final Office Action mailed Jul. 27, 2005", 15 pgs.

"U.S. Appl. No. 10/269,905, Notice of Allowance mailed Jan. 20, 2006", 11 pgs.

"U.S. Appl. No. 10/269,905, Response filed Nov. 28, 2005 to Non Final Office Action mailed Jul. 27, 2005", 13 pgs.

"U.S. Appl. No. 10/870,324, Advisory Action mailed Mar. 21, 2008", 3 pgs.

"U.S. Appl. No. 10/870,324, Examiner Interview Summary mailed Feb. 13, 2008", 4 pgs.

"U.S. Appl. No. 10/870,324, Examiner Interview Summary mailed Sep. 28, 2007", 3 pgs.

"U.S. Appl. No. 10/870,324, Examiner Interview Summary mailed Oct. 25, 2007", 3 pgs.

"U.S. Appl. No. 10/870,324, Final Office Action mailed Jan. 8, 2008", 8 pgs.

"U.S. Appl. No. 10/870,324, Non Final Office Action mailed Jun. 27, 2007", 6 pgs.

"U.S. Appl. No. 10/870,324, Non-Final Office Action mailed May 14, 2008", 8 pgs.

"U.S. Appl. No. 10/870,324, Notice of Allowance mailed Dec. 1, 2008", 7 pgs.

"U.S. Appl. No. 10/870,324, Response filed Feb. 8, 2008 to Final Office Action mailed Jan. 8, 2008", 20 pgs.

"U.S. Appl. No. 10/870,324, Response filed Aug. 14, 2008 to Non-Final Office Action mailed May 14, 2008", 22 pgs.

"U.S. Appl. No. 10/870,324, Response filed Oct. 29, 2007 to Non-Final Office Action mailed Jun. 27, 2007", 21 pgs.

"U.S. Appl. No. 10/914,496, Final Office Action mailed May 23, 2007", 11 pgs.

"U.S. Appl. No. 10/914,496, Final Office Action mailed Sep. 22, 2008", 12 pgs.

"U.S. Appl. No. 10/914,496, Non Final Office Action mailed Dec. 5, 2006", 9 pgs.

"U.S. Appl. No. 10/914,496, Non-Final Office Action mailed Mar. 18, 2008", 9 pgs.

"U.S. Appl. No. 10/914,496, Notice of Allowance mailed Jan. 16, 2009", 4 pgs.

"U.S. Appl. No. 10/914,496, Response filed Mar. 5, 2007 to Non Final office Action mailed Dec. 5, 2006", 13 pgs.

"U.S. Appl. No. 10/914,496, Response filed Jun. 18, 2008 to Non-Final Office Action mailed Mar. 18, 2008", 10 pgs.

"U.S. Appl. No. 10/914,496, Response filed Aug. 22, 2007 to Final Office Action mailed May 23, 2007", 12 pgs.

"U.S. Appl. No. 10/914,496, Response filed Nov. 24, 2008 to Final Office Action mailed Sep. 22, 2008", 9 pgs.

"U.S. Appl. No. 10/914,496, Response filed Dec. 12, 2007 to Restriction Requirement mailed Nov. 13, 2007", 7 pgs.

"U.S. Appl. No. 10/914,496, Restriction Requirement mailed Nov. 13, 2007", 5 pgs.

"U.S. Appl. No. 10/914,499, Final Office Action mailed May 12, 2009", 10 pgs.

"U.S. Appl. No. 10/914,499, Advisory Action mailed Aug. 4, 2009", 5 pgs.

"U.S. Appl. No. 10/914,499, Final Office Action mailed Jan. 24, 2008", 10 pgs.

"U.S. Appl. No. 10/914,499, Non-Final Office Action mailed Apr. 24, 2008", 5 pgs.

"U.S. Appl. No. 10/914,499, Non-Final Office Action mailed Feb. 3, 2010", 12 pgs.

"U.S. Appl. No. 10/914,499, Non-Final Office Action mailed May 29, 2007", 11 pgs.

"U.S. Appl. No. 10/914,499, Non-Final Office Action mailed on Nov. 5, 2008", 12 pgs.

"U.S. Appl. No. 10/914,499, Response filed Feb. 5, 2009 to Non-Final Office Action mailed Nov. 5, 2008", 12 pgs.

"U.S. Appl. No. 10/914,499, Response filed Apr. 14, 2008 to Final Office Action mailed Jan. 24, 2008", 11 pgs.

"U.S. Appl. No. 10/914,499, Response filed Jun. 30, 2008 to Non-Final Office Action mailed Apr. 24, 2008", 10 pgs.

"U.S. Appl. No. 10/914,499, Response filed Jul. 13, 2009 to Final Office Action mailed May 12, 2009", 10 pgs.

"U.S. Appl. No. 10/914,499, Response filed Oct. 23, 2007 to Non-Final Office Action mailed May 29, 2007", 11 pgs.

"U.S. Appl. No. 10/914,638, Final Office Action mailed Apr. 17, 2007", 10 pgs.

"U.S. Appl. No. 10/914,638, Notice of Allowance mailed Mar. 21, 2008", 4 pgs.

"U.S. Appl. No. 10/914,638, Notice of Allowance mailed Oct. 22, 2007", 4 pgs.

"U.S. Appl. No. 10/914,638, Response filed Jan. 18, 2007 to Non-Final Office Action mailed Oct. 18, 2006", 16 pgs.

"U.S. Appl. No. 10/914,638, Response filed Aug. 17, 2007 to Final Office Action mailed Apr. 17, 2007", 8 pgs.

"U.S. Appl. No. 10/914,638, Non-Final Office Action mailed Oct. 18, 2006", 9 pgs.

"U.S. Appl. No. 11/039,200, Non Final Office Action mailed Aug. 3, 2006", 10 pgs.

"U.S. Appl. No. 11/039,200, Notice of Allowance mailed Dec. 15, 2006", 4 pgs.

"U.S. Appl. No. 11/039,200, Response filed Nov. 2, 2006 to Non Final Office Action mailed Aug. 3, 2006", 9 pgs.

"U.S. Appl. No. 11/068,478, Final Office Action mailed Jun. 2, 2008", 17 pgs.

"U.S. Appl. No. 11/068,478, Non Final Office Action mailed Jan. 2, 2009", 11 pgs.

"U.S. Appl. No. 11/068,478, Non-Final Office Action mailed Dec. 17, 2007", 15 pgs.

"U.S. Appl. No. 11/068,478, Notice of Allowance mailed Jun. 9, 2009", 8 pgs.

"U.S. Appl. No. 11/068,478, Response filed Mar. 17, 2008 to Non-Final Office Action mailed Dec. 17, 2007", 19 pgs.

"U.S. Appl. No. 11/068,478, Response filed Mar. 30, 2009 to Non Final Office Action mailed Jan. 2, 2009", 20 pgs.

"U.S. Appl. No. 11/068,478, Response filed Aug. 4, 2008 to Final Office Action mailed Jun. 2, 2008", 19 pgs.

"U.S. Appl. No. 11/101,142, Non-Final Office Action mailed Jun. 20, 2007", 8 pgs.

"U.S. Appl. No. 11/101,142, Notice of Allowance mailed Nov. 27, 2007", 5 pgs.

"U.S. Appl. No. 11/101,142, Response filed Jun. 6, 2007 to Restriction Requirement Response mailed May 3, 2007", 7 pgs.

"U.S. Appl. No. 11/101,142, Response filed Sep. 20, 2007 to Non-Final Office Action mailed Jun. 20, 2007", 7 pgs.

"U.S. Appl. No. 11/101,142, Restriction Requirement mailed May 3, 2007", 5 pgs.

"U.S. Appl. No. 11/101,196, Non Final Office Action mailed Mar. 29, 2007", 8 pgs.

"U.S. Appl. No. 11/101,196, Notice of Allowance mailed Aug. 27, 2007", 5 pgs.

"U.S. Appl. No. 11/101,196, Response filed Jun. 29, 2007 to Non Final Office Action mailed Mar. 29, 2007", 8 pgs.

"U.S. Appl. No. 11/116,108, Advisory Action mailed Jan. 29, 2009", 3 pgs.

"U.S. Appl. No. 11/116,108, Final Office Action mailed Oct. 10, 2008", 7 pgs.

"U.S. Appl. No. 11/116,108, Non-Final Office Action mailed Mar. 20, 2008", 11 pgs.

"U.S. Appl. No. 11/116,108, Non-Final Office Action mailed Apr. 23, 2009", 7 pgs.

"U.S. Appl. No. 11/116,108, Notice of Allowance mailed Sep. 29, 2009", 8 pgs.

"U.S. Appl. No. 11/116,108, Response filed Jul. 23, 2009 to Non Final Office Action mailed Apr. 23, 2009", 7 pgs.

"U.S. Appl. No. 11/116,108, Response filed Dec. 10, 2008 to Final Office Action mailed Oct. 10, 2008", 6 pgs.

"U.S. Appl. No. 11/116,108, Response filed Jun. 20, 2008 to Non-Final Office Action mailed Mar. 20, 2008", 9 pgs.

"U.S. Appl. No. 11/244,273, Notice of Allowance mailed Oct. 5, 2009", 7 pgs.

"U.S. Appl. No. 11/244,273, Non-Final Office Action mailed on Nov. 28, 2008", 7 pgs.

"U.S. Appl. No. 11/244,273, Response filed Aug. 12, 2009 to Ex Parte Quayle mailed Jun. 12, 2009", 4 pgs.

"U.S. Appl. No. 11/244,273, Response filed Oct. 22, 2008 to Restriction Requirement mailed Jul. 22, 2008", 13 pgs.

"U.S. Appl. No. 11/244,273, Response filed Mar. 2, 2009 to Non-Final Office Action mailed Nov. 28, 2008", 13 pgs.
"U.S. Appl. No. 11/244,273, Restriction Requirement mailed Jul. 22, 2008", 10 pgs.
"U.S. Appl. No. 11/325,564, Examiner Interview Summary mailed Jun. 24, 2009", 2 pgs.
"U.S. Appl. No. 11/325,584, Final Office Action mailed Oct. 24, 2008", 5 pgs.
"U.S. Appl. No. 11/325,584, Non-Final Office Action mailed Mar. 24, 2009", 5 pgs.
"U.S. Appl. No. 11/325,584, Non-Final Office Action mailed Apr. 10, 2008", 6 pgs.
"U.S. Appl. No. 11/325,584, Notice of Allowance mailed Oct. 21, 2009", 5 pgs.
"U.S. Appl. No. 11/325,584, Response filed Jan. 22, 2009 to Final Office Action mailed Oct. 24, 2008", 6 pgs.
"U.S. Appl. No. 11/325,584, Response filed Jun. 24, 2009 to Non Final Office Action mailed Mar. 24, 2009", 9 pgs.
"U.S. Appl. No. 11/325,584, Response filed Jul. 10, 2008 to Non Final Office Action mailed Apr. 10, 2008", 9 pgs.
"U.S. Appl. No. 11/381,493, Appeal Brief filed Nov. 16, 2009", 19 pgs.
"U.S. Appl. No. 11/381,493, Final Office Action mailed Jan. 8, 2009", 12 pgs.
"U.S. Appl. No. 11/381,493, Final Office Action mailed Apr. 16, 2009", 14 pgs.
"U.S. Appl. No. 11/381,493, Non-Final Office Action mailed Jun. 23, 2008", 13 pgs.
"U.S. Appl. No. 11/381,493, Response filed Mar. 9, 2009 to Final Office Action mailed Jan. 8, 2009", 13 pgs.
"U.S. Appl. No. 11/381,493, Response filed Apr. 28, 2008 to Restriction Requirement mailed Mar. 26, 2008", 9 pgs.
"U.S. Appl. No. 11/381,493, Response filed Jun. 9, 2009 to Final Office Action mailed Apr. 16, 2009", 13 pgs.
"U.S. Appl. No. 11/381,493, Response filed Sep. 22, 2008 to Non-Final Office Action mailed Jun. 23, 2008", 15 pgs.
"U.S. Appl. No. 11/381,493, Restriction Requirement mailed Mar. 26, 2008", 7 pgs.
"U.S. Appl. No. 11/640,552, Response filed Aug. 11, 2009 to Non Final Office Action mailed May 11, 2009", 10 pgs.
"U.S. Appl. No. 11/733,339, Non Final Office Action mailed Apr. 30, 2009", 10 pgs.
"U.S. Appl. No. 11/733,339, Non-Final Office Action mailed Sep. 9, 2009", 9 pgs.
"U.S. Appl. No. 11/733,339, Response filed Dec. 4, 2009 to Non Final Office Action mailed Sep. 9, 2009", 11 pgs.
"U.S. Appl. No. 11/914,499, Response filed Nov. 10, 2009 to Advisory Action mailed Aug. 4, 2009", 12 pgs.
"European Application No. 02799254.4 Office Action Mailed Sep. 23, 2009", 4 pgs.
"European Application No. 05783799.9 , Communication pursuant to Article 94(3) EPC mailed on Jun. 16, 2009", 3 pgs.
"European Application No. 05783882.3 , Communication pursuant to Article 94(3) EPC mailed Jun. 16, 2009", 3 pgs.
"International Application No. PCT/US2002/040488, International Search Report mailed May 9, 2003", 7 pgs.
"International Application No. PCT/US2003/003748, International Search Report mailed Oct. 20, 2003", 5 pgs.
"International Application No. PCT/US2005/011606, International Search Report and Written Opinion mailed Jul. 26, 2005", 12 pgs.
"International Application No. PCT/US2005/011639, International Search Report and Written Opinion mailed Aug. 26, 2005", 12 pgs.
"International Application No. PCT/US2005/028052, International Preliminary Report on Patentability mailed Feb. 22, 2007", 8 pgs.
"International Application No. PCT/US2005/028052, International Search Report and Written Opinion for date mailed Nov. 29, 2005", 12 pgs.
"International Application No. PCT/US2005/028052, International Search Report and Written Opinion mailed Nov. 29, 2005", 12 pgs.
"International Application No. PCT/US2005/028059, International Preliminary Report on Patentability mailed Feb. 13, 2007", 9 pgs.
"International Application No. PCT/US2005/028059, International Search Report and Written Opinion mailed Dec. 1, 2005.", 13 pgs.
"International Application No. PCT/US2005/028059, International Search Report and Written Opinion mailed Jan. 12, 2005", 13 pgs.
"International Application No. PCT/US2006/014957, International Search Report and Written Opinion mailed Sep. 29, 2006", 16 pgs.
"International Application No. PCT/US2007/069424, International Search Report mailed Dec. 27, 2007", 4 pgs.
"International Application No. PCT/US2007/069424, Written Opinion mailed Dec. 27, 2007", 9 pgs.
"International Application No. PCT/US2007/069426, International Search Report mailed Dec. 27, 2007", 4 pgs.
"International Application No. PCT/US2007/069426, Written Opinion mailed Dec. 27, 2007", 8 pgs.
"International Application No. PCT/US2007/072827, International Search Report mailed Dec. 10, 2007", 4 pgs.
"International Application No. PCT/US2007/072827, Written Opinion mailed Dec. 10, 2007", 6 pgs.
"Part III—Department of Health and Human Services, Office of the Secretary—45 CFR Part 142—Security and Electronic Signature Standards; Proposed Rule", *Federal Register*, 63(155), (Aug. 12, 1998), 43241-43280.
"Public Law 104-191 [H.R. 3103]—Health Insurance Portability and Accountability Act of 1996", *United States Public Laws—104th Congress—2nd Session*, (Aug. 21, 1996), 78 pgs.
Bange, Joseph E, et al., " U.S. Appl. No. 11/101,196, filed Apr. 7, 2005", 19 pgs.
Diffie, W., "The First Ten Years of Public-Key Cryptography", *Proceedings of the IEEE*, 76(5), (May 1988), 560-577.
Golmie, N., et al., "The Evolution of Wireless LANs and PANs—Bluetooth and WLAN coexistence: challenges and solutions", *IEEE Personal Communications*, 10(6), (Dec. 2003), 22-29.
Guidant, "Feature Sheet and Specifications: Zoom Latitude", Doc. No. C3-194-1005, (2005), 2 pgs.
Guidant, "Go Beyond the Wand", Doc. No. C3-107-0505, (2005), 2 pgs.
Guidant, "Think Beyond the Wand", Doc. No. C3-101-0505, (2005), 3 pgs.
Guidant, "What if you could ZIP through implants and follow ups?", Doc. No. C3-117-0505, (2005), 2 pgs.
Guidant, "What if your patient develops diaphragmatic stimulation?", Doc. No. C3-116-0505, (2005), 2 pgs.
Harney, Austin, et al., "Wireless Short-Range Devices: Designing a Global License-Free System for Frequencies <1 GHz", *Analog Dialogue 40-03*, (Mar. 2006), 1 pg.
Katoozi, M., et al., "U.S. Appl. No. 10/870,328, filed Jun. 17, 2004", 30 pgs.
Quiles, S., "U.S. Appl. No. 10/914,499, filed Aug. 9, 2004", 30 pgs.
Quiles, Sylvia, "U.S. Appl. No. 10/914,496, filed Aug. 9, 2004", 23 pgs.
Rawat, Prashant, et al., "U.S. Appl. No. 10/744,943, filed Dec. 22, 2003", 34 pgs.
Seeberger, M., "U.S. Appl. No. 10/914,638, filed Aug. 9, 2004", 35 pgs.
Von Arx, Jeffrey, "U.S. Appl. No. 10/870,324, filed Jun. 14, 2004", 38 pgs.
"U.S. Appl. No. 10/914,499, Notice of Allowance mailed Sep. 29, 2010", 4 pgs.
"U.S. Appl. No. 10/914,499, Response filed May 3, 2010 to Non-Final Office Action mailed Feb. 3, 2010", 12 pgs.
"U.S. Appl. No. 10/914,499, Response filed Aug. 31, 2010 to Final Office Action mailed Jul. 20, 2010", 10 pgs.
"U.S. Appl. No. 11/325,584, Notice of Allowance mailed Mar. 23, 2010", 4 pgs.
"U.S. Appl. No. 11/381,493, Examiner's Answer mailed Mar. 25, 2010", 20 pgs.
"U.S. Appl. No. 11/381,493, Reply Brief filed Apr. 29, 2010", 6 pgs.
"U.S. Appl. No. 12/102,480, Final Office Action mailed Jan. 18, 2011", 6 pgs.
"U.S. Appl. No. 12/102,480, Non-Final Office Action mailed Aug. 18, 2010", 9 pgs.
"U.S. Appl. No. 12/102,480, Response filed Apr. 18, 2011 to Final Office Action mailed Jan. 18, 2011", 9 pgs.
"U.S. Appl. No. 12/102,480, Response filed Nov. 18, 2010 to Non-Final Office Action mailed Aug. 18, 2010", 13 pgs.

"U.S. Appl. No. 12/435,928, Non-Final Office Action mailed Oct. 22, 2010", 14 pgs.

"U.S. Appl. No. 12/435,928, Notice of Allowance mailed May 4, 2011", 9 pgs.

"U.S. Appl. No. 12/435,928, Response filed Jan. 21, 2011 to Non Final Office Action mailed Oct. 22, 2010", 13 pgs.

"U.S. Appl. No. 12/648,687, Notice of Allowance mailed Apr. 17, 2010", 7 pgs.

"U.S. Appl. No. 12/684,303, Non-Final Office Action mailed Apr. 5, 2011", 5 pgs.

"European Application Serial No. 05783799.9, Office Action mailed Oct. 25, 2010", 3 pgs.

"European Application Serial No. 05783799.9, Response filed May 3, 2011 to Office Action mailed Oct. 25, 2010", 12 pgs.

"European Application Serial No. 05783799.9, Response filed Oct. 23, 2009 to Communication mailed Jun. 16, 2009", 9 pgs.

"Japanese Application Serial No. 2007-525697, Office Action mailed Apr. 19, 2011", (w/ English Translation), 7 pgs.

* cited by examiner

TELEMETRY DUTY CYCLE MANAGEMENT SYSTEM FOR AN IMPLANTABLE MEDICAL DEVICE

CROSS-REFERENCE TO RELATED APPLICATIONS

This application is a continuation of U.S. patent application Ser. No. 11/325,584, filed on Jan. 4, 2006, now issued as U.S. Pat. No. 7,738,964, which is a continuation of U.S. patent application Ser. No. 10/025,223, filed on Dec. 19, 2001, now issued as U.S. Pat. No. 6,993,393, the specifications of which are incorporated herein by reference.

TECHNICAL FIELD

In general, the present subject matter relates to implantable medical devices, such as cardiac pacemakers and cardioverter/defibrillators, and in particular, the present subject matter relates to wireless telemetry with implantable medical devices.

BACKGROUND

Implantable medical devices, including cardiac rhythm management devices such as pacemakers and implantable cardioverter/defibrillators, typically have the capability to communicate data with a device called an external programmer, or programmer, via a radio frequency telemetry link. A clinician may use such a programmer to program the operating parameters of an implanted medical device. For example, the pacing mode and other operating characteristics of a pacemaker may be modified after implantation in this manner. Modern implantable medical devices also include the capability for bidirectional communication so that information can be transmitted to the programmer from the implanted device. Among the data which may be telemetered from an implantable medical device are various operating parameters and physiological data, the latter either collected in real-time or stored from previous monitoring operations.

Telemetry systems for implantable medical devices may utilize radio frequency (RF) energy to enable bidirectional communication between the implantable medical device and an external programmer. In some applications, a wireless RF carrier is modulated with digital information, typically by amplitude shift keying where the presence or absence of pulses in the signal constitute binary symbols or bits. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. The external programmer transmits and receives the radio signal with an antenna incorporated into a wand that can be positioned in proximity to the implanted device. The implantable medical device also generates and receives radio signals by means of an antenna, which may include a wire coil inside of the device casing.

Some RF telemetry systems used for implantable medical devices, such as cardiac pacemakers, utilize inductive coupling between the antennas of the implantable medical device and an external programmer in order to transmit and receive wireless signals. Because the induction field produced by a transmitting antenna falls off rapidly with distance, such systems require close proximity between the implantable medical device and a wand antenna of the external programmer in order to work properly, usually on the order of a few inches. This requirement is inconvenient for the patient and the clinician, and thereby limits the situations in which telemetry can take place.

SUMMARY OF THE INVENTION

The present invention includes a system and method for managing the duty cycles of RF telemetry components in an implantable medical device and an external device in order to lessen power consumption. In accordance with the invention, the RF telemetry circuitry of both devices is maintained in a quiescent or powered down state and powered up at predetermined time intervals. According to one embodiment, in a powered down state, the electric current is reduced and in a powered up state, the electric current is raised to allow reception or transmission of RF energy.

One of the devices is designated as the master device and configured to transmit a digital key when the RF circuitry is powered up in an attempt to establish a communications session with the other device. The other device is designated as the slave device and configured to listen for the digital key when its RF circuitry is powered up and transmit a response if the digital key is received. A communications session is then begun, and the circuitry of both devices remains powered up until the session is finished. When no communications sessions are taking place, the duty cycle of the RF circuitry in each device is thus reduced to only the time spent in transmitting or listening for the digital signature. In a preferred embodiment, the external device is configured as the master device while the implantable medical device is configured as the slave device.

In addition, the present subject matter includes, among other things, a system having an implantable medical device having multiple means for wireless communication. In one embodiment, the system communicates using two independent means, each adapted for a particular function. For example, one embodiment includes a near field wireless communication means, such as an inductive coupling, as well as a far field wireless communication means, such as a far field RF coupling.

The present subject matter includes, among other things, an apparatus and method for enabling communications with an implantable medical device utilizing a near field inductive coupling and far field electromagnetic radiation. In one embodiment, communications in a clinical setting may be conducted using either the inductive coupling or the far field radiation coupling. Communications over a greater distance, in general, are conducted using the far field radiation coupling.

In accordance with one embodiment, a conductor coupled to the implantable medical device serves as an antenna that transmits and receives far field RF radiation modulated with telemetry data. The antenna is adapted to transmit far field radiation at a particular frequency. In one embodiment, a tuning circuit is used to adjust the impedance, and thereby tune the antenna to a particular frequency. In one embodiment, a therapy lead of a cardiac rhythm management device, which is otherwise used for stimulating or sensing electrical activity in the heart, has, incorporated therein, a wire antenna. In one embodiment, a specialized structure is incorporated into such a therapy lead in order to isolate a separate antenna section therein. In one embodiment, the antenna includes a helix structure located proximate to, or internal to, a housing of the medical device. In one embodiment, the antenna includes a wire disposed around the circumference of the outer surface of the device housing.

In one embodiment, a near field coupling includes an implanted coil of wire. The implanted coil is tailored and aligned for inductive coupling with an external coil. In one embodiment, the coils are coupled by electromagnetic coupling.

In one embodiment, the system includes a timer function that allows far field communications to be enabled for a limited duration. In one embodiment, for example, a clinician marks the beginning of a programming period by transmitting a near field signal using a programmer wand. During the programming period, the far field section of the implantable medical device is engaged, and powered, and can receive programming instructions without using a wand. At the expiration of the programming period, the far field section is disabled. In one embodiment, the near field section remains continuously available and operates independent of the far field section. In one embodiment, the data received by the far field section is installed and executed immediately after receipt. In one embodiment, after transmitting updated parameters or program instructions, the clinician then uses the near field section to transmit an update command which causes the implantable medical device to implement the replacement parameters or program instructions.

Upon receiving an update command at the implantable medical device, the received data is transferred from a first memory location to a second memory location. Instructions, or data, stored in the second memory location controls the operation of the implantable medical device. For example, configuration statements or data can be communicated to the implantable medical device and initially stored in a temporary memory location and after receiving an update command, the contents of the temporary location are transferred to a semi-permanent memory location for execution and implementation.

In one embodiment, the near field communication section is used to signal to the implantable medical device that selected functions are available. In various embodiments, the selected functions include interrogation functions or programming functions. For example, in one embodiment, the implantable medical device transmits status information according to a predetermined schedule. In various embodiments, the status information is transmitted using either the far field transmitter, the near field transmitter, or both. In one embodiment, the far field receiver section normally remains in an unpowered mode and after receiving a near field transmission, the far field receiver is powered and data received is stored in a memory. In one embodiment, the far field receiver is ordinarily unpowered and transitions to a powered mode upon receipt of a near field signal. The receipt of the near field signal marks the beginning of a period during which a predetermined programming or interrogation function is available. During the period before receiving the near field signal, and during the period after the predetermined period, the programming or interrogation function is not available.

Other means of programming, interrogating and communicating with the implantable medical device are also contemplated. For example, in one embodiment, a far field communication including a particular message marks the opening of a window during which both far or near field communications may be subsequently conducted.

As another example, one embodiment includes an implanted medical device having a far field transceiver operated according to a predetermined duty cycle and a programmer having a complementary far field transceiver, also operated according to a predetermined duty cycle. In such an embodiment, the medical device and the programmer are configured to communicate on a peer-to-peer basis and not on the basis of a master-slave relationship. In one embodiment of the peer-to-peer system, the medical device and the programmer are cycled in phase according to a predetermined schedule. In one embodiment, the medical device is operated according to a first duty cycle and the programmer is operated according to a second duty cycle or operated continuously.

DETAILED DESCRIPTION

The present invention includes a system and method for providing far-field RF telemetry between an implantable medical device and an external device in which power consumption is lessened by managing the duty cycles of the RF transmitting and receiving components. As used herein, the term data includes digital data and analog signals.

Figure 1:
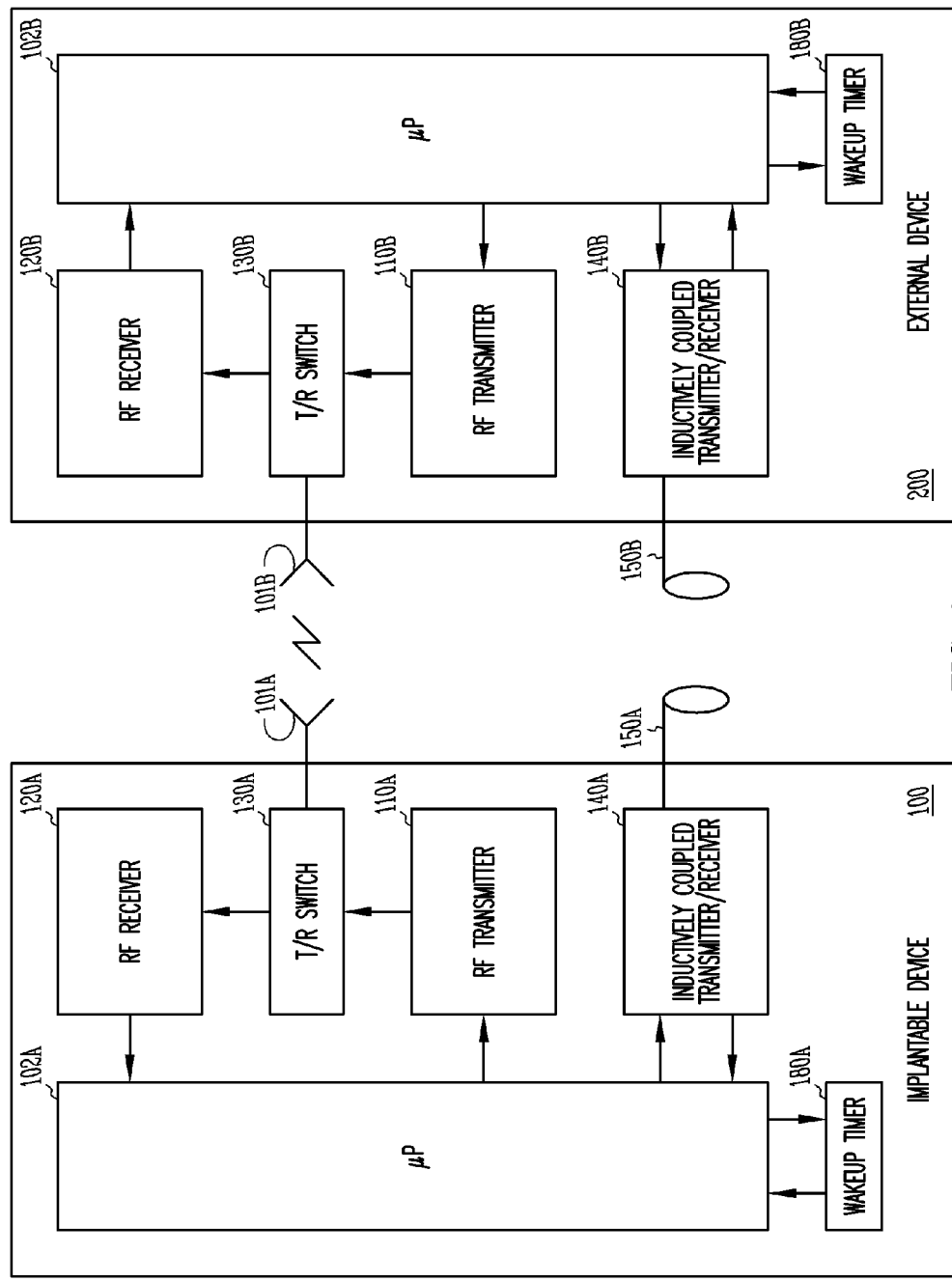
FIG. 1 is a block diagram of a telemetry system for an implantable medical device and an external device.

FIG. 1 shows selected telemetry components of external device 200 and implantable medical device 100. In this functional block diagram, the components are shown as being substantially identical in each device, however, in one embodiment, the components differ. In this exemplary embodiment, implantable medical device 100 and external device 200 are microprocessor-based devices with implantable medical device 100 having controller 102A and external device 200 having controller 102B. Controllers 102A and 102B each include a microprocessor and memory for data and program storage that supervises overall device operation as well as telemetry. In one embodiment, the code executed by controllers 102A and 102B also implements the duty cycle management schemes to be described below. Implantable medical device 100, in one embodiment, includes a cardiac rhythm management device such as a pacemaker or implantable cardioverter/defibrillator, and external device 200 includes a data-gathering device such as an external programmer or remote monitor. In one embodiment, both device 100 and device 200 are battery powered. In one embodiment, device 200 is powered by a metered line service.

In one embodiment, long-range RF receivers 120A, and 120B, and long-range RF transmitters 110A, and 110B, are interfaced to microprocessors 102A, and 102B, in implantable medical device 100 and external device 200, respectively. In one embodiment, transmitters 110A, and 110B, and receivers 120A, and 120B, are coupled to antennas 101A, and 101B, through transmit/receive switches 130A and 130B, respectively. Switches 130A and 130B are controlled by controllers 102A and 102B, respectively. Switch 130A passes RF signals from transmitter 110A to antenna 101A or from antenna 101A to receiver 120A. Switch 130B passes RF signals from transmitter 110B to antenna 101B or from antenna 101B to receiver 120B. To effect communications between devices 100 and 200, an RF carrier signal modulated with digital data is transmitted wirelessly from one antenna to the other. In one embodiment, a demodulator for extracting digital data from the carrier signal is incorporated into receivers 120A and 120B, and a modulator for modulating the carrier signal with digital data is incorporated into transmitters 110A and 110B. In one embodiment, an interface coupled to controller 102A and RF transmitter 110A, and controller 102A and receiver 120A in device 100 enables data transfer and also provides a means by which controller 102A can power up or power down receiver 120A or transmitter 110A and thus manage duty cycles in the manner described below. In one embodiment, an interface coupled to controller 102B and RF transmitter 110B, and controller 102B and receiver 120B in device 200 enables data transfer and also provides a means by which controller 102B can power up or power down receiver 120B or transmitter 110B and thus manage duty cycles in the manner described below. In one embodiment, wakeup timers 180A and 180B are coupled to controllers 102A, and 102B, respectively. Timers 180A and 180B define the duty cycles and, in one embodiment, are implemented in code executed by the respective controller and, in one embodiment, include discrete components.

Far field telemetry over greater distances can be achieved by wireless RF communication. The ability to communicate over a greater distance may be advantageous for the patient as well as the clinician. The increased communication range makes possible other applications of the telemetry system such as remote monitoring of patients and communication with other types of external devices. To emit a substantial portion of the energy delivered to an antenna as far field radiation, preferably, the wavelength of the driving signal is not much larger than the length of the antenna. Far-field radio frequency communications with an antenna of a size suitable for use in an implantable medical device therefore can be conducted using a carrier frequency in the range between a few hundred MHz to a few GHz. Active transmitters and receivers for this frequency range employ special RF components (which may include SiGe or GaAs semiconductor devices) that consume a significant amount of power (typically tens of milliwatts). Implantable medical devices, however, are powered by a battery contained within the housing of the device that can only supply a limited amount of continuous power before it fails. When the battery fails in an implantable medical device, it must be replaced which necessitates a reimplantation procedure. Portable external devices may also be battery powered, and recharging or replacement of the battery in such devices is an inconvenience.

Long-range RF telemetry circuitry (i.e., the transmitter and receiver) typically requires power on the order of tens of milliwatts in order to operate. Cardiac rhythm management devices in use today, on the other hand, are usually designed to operate with average power in the microwatt range. Thus, to meet the power budget of such devices, the RF telemetry circuitry is preferably duty cycled down by about four orders of magnitude. An example of duty cycling for an implantable medical device is described in U.S. Pat. No. 5,342,408, presently assigned to the Guidant Corp. and hereby incorporated by reference. External devices, although not subject to the same power constraints as implantable medical devices, may be portable and battery powered. Duty cycling down the RF circuitry in external devices may advantageously avoid the inconvenience of premature battery depletion. In one embodiment, implantable medical device 100 employs a power management scheme in which RF receiver 120A and RF transmitter 110A are duty cycled based upon synchronized timer wakeups. In one embodiment, external device 200 employs a power management scheme in which RF receiver 120B and RF transmitter 110B are duty cycled based upon synchronized timer wakeups.

In such a scheme, the RF telemetry circuitry is normally in a low power state until powered up to transmit or receive a message. In one embodiment, the controller in the implantable medical device and the controller in the external device are both programmed to maintain the RF circuitry in a quiescent or powered down state and then power up the circuitry at programmable time intervals based upon timer expirations or other conditions.

In one embodiment, one of the devices is designated as the slave device. After a programmable wakeup time interval, the RF receiver in the slave device is powered up for a specified slave time window and listens for a valid digital key transmitted by another device designated as the master device. The master device, after a programmable wakeup time interval, also powers up its RF transmitter and receiver for a specified master time window to transmit the digital key and listen for a response from the slave device. If no valid digital key is received, the slave device powers down the RF receiver until the next wakeup interval. If a valid digital key is received, the slave device powers up its RF transmitter and responds by transmitting a response code to the master device to initiate a communications session.

In one embodiment, the slave device receives a digital key without initiating a communications session, in which case the reception of the key is used for timing or other purposes by the slave device. In one embodiment, different digital keys are used to differentiate between situations where the slave is obligated to respond and initiate a communications session with the master device and situations where the slave has the option to respond or not. If a communications session is established, the RF circuitry in both the slave and master devices remains powered up until the session is finished, and then the RF circuitry in each device is powered down until the next wakeup interval.

In one embodiment, the external device is configured as the master device while the implantable medical device is configured as the slave device. This configuration may be less burdensome on the implantable medical device's more limited battery power supply since periodically powering up the RF receiver to listen for a digital key may draw less current than powering up both the RF transmitter and RF receiver to transmit a digital key and listen for a response. In addition, in certain situations, it may be undesirable for the implantable medical device to transmit an RF signal. For example, a patient may be onboard a commercial airplane or in a country where regulations prohibit RF transmissions at the system frequency. If the implantable medical device is the slave, then unless a digital key is received, the implantable medical device will not broadcast an RF transmissions.

In one embodiment, the programmable wakeup time intervals for the master and slave devices are synchronized so that they occur simultaneously. As long as the devices are located within range, a communications session would then be established at every such wakeup interval.

In one embodiment, synchronization of the wakeup timers is performed during any communications session established with the RF telemetry link. Synchronization can be done by a variety of means. In one embodiment, synchronization entails having one device transmit a time stamp and having the other device adjust its timer accordingly. In one embodiment, the receiving device synchronizes by detecting a start of a message and realigning its wakeup interval to begin at the same time. In one embodiment, synchronization of the timers is performed using inductive coupling. In one embodiment, an inductively coupled link is used to transmit a magnetic pulse that activates a switch or is otherwise detected by the receiving device, and the device is then programmed to synchronize its wakeup timer at that time by setting it to a predetermined value.

Another alternative is for a communications session to be established with an inductively coupled link such as used in conventional short-range telemetry. FIG. 1 shows inductively coupled transceivers 140A and 140B, each coupled to antennas 150A and 150B, respectively, for each of the implantable medical device and external device. Transceivers 140A and 140B, and antennas 150A and 150B, draw low power, and in one embodiment, are operated continuously. In this manner, a communications link can be established immediately without waiting for a wakeup interval.

Whatever means are used to establish a communications session, the wakeup timers of the master and slave devices can be synchronized and a programmable wakeup interval agreed upon by the two devices during the session. The wakeup interval can be a fixed value set by clinician input or can be made to vary in accordance with detection of particular events. For example, when the implantable medical device includes a cardiac rhythm management device and an arrhythmia is detected, the implantable medical device can be programmed to increase the frequency at which communications sessions occur in order to more closely monitor the patient. This is accomplished by the implantable medical device reducing the wakeup interval for each device when a communications session with an external device is next established.

In one embodiment, the frequency of communications sessions is increased by reducing the wakeup interval when the implantable medical device detects a low battery condition or a change in lead impedance. Increasing the frequency of communication sessions allows the operating status of the implantable medical device to be more frequently communicated to the external device. In one embodiment, clinician input from an external programmer can be used to change the wakeup interval of the implantable medical device. In one embodiment, the wakeup interval is varied pseudo-randomly from one communications session to another. Pseudo-random variability may be desirable in order to minimize the chance of periodic interference from an external source or other devices causing transmission problems.

In one embodiment, each slave device has a unique digital key and a single master device can thus, individually, access each slave. This configuration prevents two slave devices from interfering with each other by responding to a digital key transmitted from the master device. In one embodiment, a slave device is programmed to respond to a digital key used in common with one or more other devices. For example, in one embodiment, a digital key is uniquely specified for a family of slave devices. In that case, the possibility of interference can be lessened by programming the slave device to respond to a digital key after a random delay time.

In one embodiment, the timing of the master device is perfectly synchronized with the timing of the slave device. That is, the power up times for the receiver in the slave device and both the transmitter and receiver of the master device are precisely defined. Precise definition of the power up times allows the duty cycles of the RF circuitry to be minimized, thus reducing power consumption.

It may be found that timing drift prevents perfect synchronization of the wakeup intervals. In one embodiment, the master time window begins at some time before the slave time window starts. That is, the master device begins transmitting the digital key shortly before the slave device is expected to be listening for it. In one embodiment, the master time window extends beyond the slave time window such that if no response from the slave is received, the master continues transmitting the digital key until after the slave is expected to no longer be listening. In one embodiment, the listening time of the slave or slave time window is great enough to receive at least two digital keys so that if it just misses the start of a key transmitted by the master, the next transmitted key will be received in its entirety. This technique thus increases the probability that communication between the devices will be established even when timing drift occurs. Because the master device transmits and receives for a longer period of time than the slave device listens, there is a greater energy burden on the master device. In one embodiment, the implantable medical device, with its more severe battery constraints, is configured as the slave device.

In one embodiment, the wakeup timers are synchronized (or resynchronized) automatically during each communication session. Resynchronizing during each communication session reduces the amount of desynchronization that exists between the timers of the master and slave devices (due to timing drift). In one embodiment, the device receiving the time stamp attempts to compensate for the amount of drift that occurred since the last communications session. At each such session, the device receiving the time stamp stores the amount by which it had to adjust its wakeup timer and thus learns the average amount of timer drift that occurs between the timers of both devices. The device is programmed to set its wakeup timer either ahead or behind that of the wakeup timer of the other device if it was slow or fast, respectively, relative to that timer. The amount by which the timer is set ahead or behind that of the other timer can be made either equal to the amount of drift or some fraction of it.

In one embodiment, the master device adjusts the time window used to transmit the digital key and listen for a response at each wakeup interval based on the average amount of timer drift. In one embodiment, the master device adjusts the time window based on the time since the last resynchronization. In one embodiment, the master device begins transmitting the digital key before it anticipates that the slave device will be listening for it, and continues transmitting the key until after it anticipates that the slave device has powered down its receiver. This helps to ensure that the master device will catch the slave device listening even if the timers of the two devices have drifted relative to one another. The amount of drift between the two wakeup timers will increase as a function of the time since the last resynchronization. The amount of energy that the master device spends in attempting to establish a communications session can therefore be reduced by making the duration of the transmitting and listening time window a function of the time since the last resynchronization.

Consider the following example. Assume that the wakeup timers of the master and slave devices were last resynchronized 100 seconds ago. At the next wakeup interval, the master device could anticipate that the drift of the wakeup timers would be rather small, and therefore, the master device can reliably begin sending the digital key to the slave device only a few tens of microseconds before it anticipates that the slave will be listening. On the other hand, if the wakeup timers of the master and slave devices were last resynchronized eight hours (28,800 seconds) ago, then it is likely that the drift will be 288 times greater than had it been resynchronized 100 seconds ago. Thus, at the next wakeup interval, the master device should begin sending the digital key to the slave device a few tens of milliseconds before it anticipates that the slave will be listening.

In one embodiment, the master device is configured to conduct a search for a non-synchronized slave receiver. A slave receiver may be non-synchronized for any of a number of reasons. For example, but not by way of limitation, the slave receiver may be newly implanted in a particular patient, the batteries of the master device may have just been changed, or the master device may not have been used recently. In one embodiment, the master and slave devices are resynchronized using an inductive telemetry link as described above.

Consider an example where the master device has not successfully established a communications session with a particular slave device for a specified maximum period of time (e.g., 4 hours). In this case, the master device will assume that the slave device is not synchronized, and the master device will begin a non-synchronized receiver search. In one embodiment, the master device continuously transmit its digital key and listen for a response until either a communications session is established or a programmable maximum non-synchronized search interval (e.g., 200 seconds) passes. If a communications session is established, the wakeup timers of the two devices are resynchronized. If the maximum non-synchronized search interval passes with no communications session being established, then the master device assumes that no slave device is within range and goes back to its previous wakeup interval pattern. If the specified maximum time with no communications session being established again passes (e.g., another 4 hours), the non-synchronized receiver search is repeated. In one embodiment, the master device keeps track of the expected slave device wakeup windows during a non-synchronized receiver search so that the master device can return to these if no non-synchronized slave device is found.

In the systems described above, the RF circuitry of both the implantable and external devices are duty cycled in order to lessen power consumption, with one device operating as a slave and the other device operating as a master. In one embodiment, the devices are programmed such that one device is always configured as the master device while the other device is programmed to always be configured as the slave device. In one embodiment, the devices are programmed to dynamically configure themselves as either master or slave devices depending upon circumstances. For example, in one embodiment, both the implantable and external devices are programmed to normally act as slave devices such that they both wake up at periodic intervals to listen for a communications session request from the other device. Upon a change in circumstances, such as clinician input to the external device or detection of a particular event by the implantable medical device, one of the devices configures itself as a master to request a communications session at the next wakeup interval. In order to deal with the situation where both devices configure themselves as master devices, in one embodiment, the system incorporates a mediation scheme like those employed in peer-to-peer networks.

In one embodiment, the RF circuitry of the master device is duty cycled and that of the slave device is continuously powered. In one embodiment, the RF circuitry of the slave device is duty cycled and that of the master device is continuously powered. Such a configuration may be beneficial, for example, if one device has unusually severe battery constraints or is intended for very limited use while the other device has access to continuous power. In such a system, the duty cycled device is configured to operate as either a master or slave device in establishing communications sessions with the continuously powered up device. In one embodiment, the duty cycled device is configured as a slave in order to lessen its power requirements somewhat. The continuously powered device, acting as a master, then periodically powers up its RF circuitry at programmed wakeup intervals in order to attempt to initiate a communications session with the duty cycled device.

Figure 2:
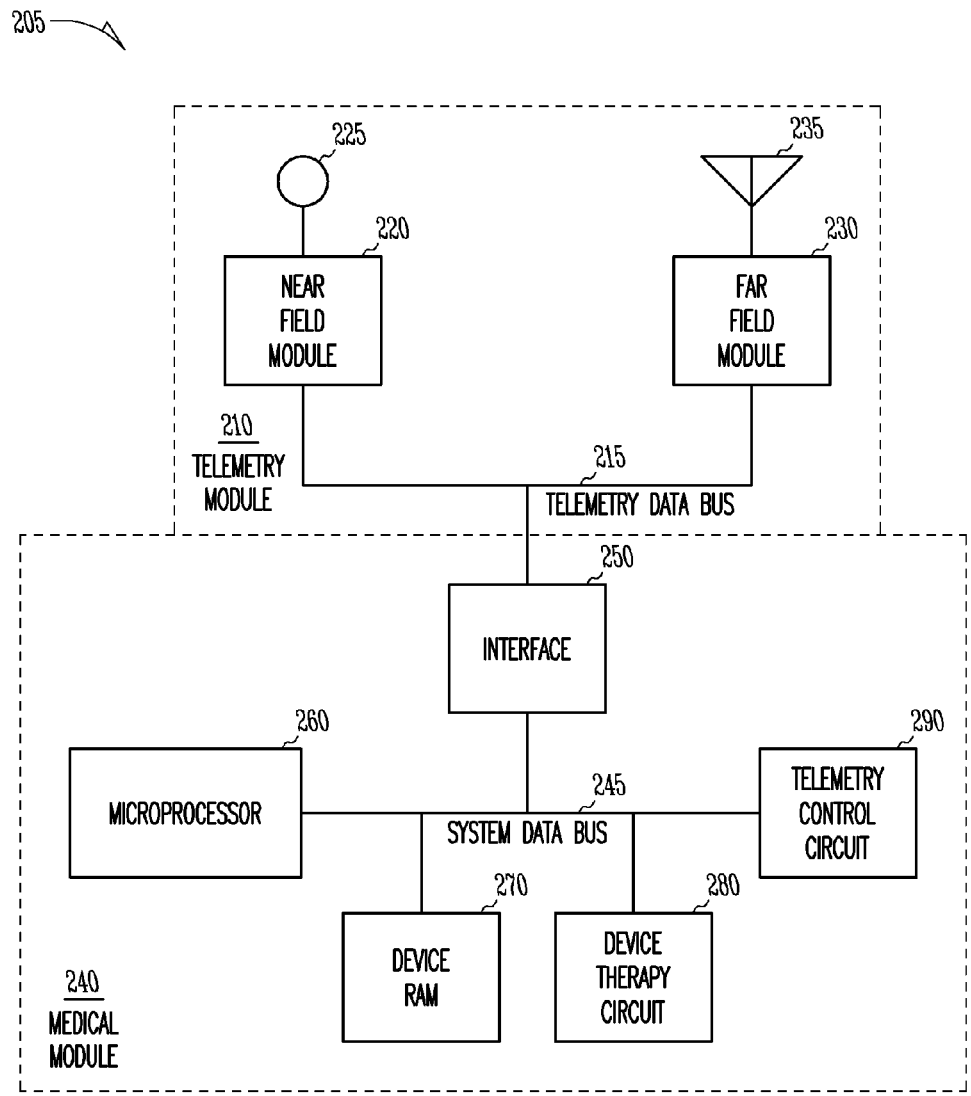
FIG. 2 is a block diagram view of an embodiment of an implantable medical device having both a near field module and a far field module.

FIG. 2 illustrates an embodiment of an implantable medical device 205 having telemetry module 210 coupled to medical module 240. In one embodiment, implantable medical device 205 is housed in a sealed canister suited for implantation in a human body. Telemetry module 210 includes near field module 220 and far field module 230. Near field module 220 and far field module 230 are coupled together by telemetry data bus 215. In various embodiments, bus 215 includes a digital data bus or an analog signal line. Near field module 220 is coupled to antenna 225, herein depicted by a loop, or coil. In one embodiment, antenna 225 includes an inductive loop. Far field module 230 is coupled to antenna 235, herein depicted by an RF antenna. In one embodiment, antenna 235 includes a dipole antenna. In one embodiment, antenna 235 includes a monopole antenna.

Antenna 235 may include a circumferential antenna disposed around an exterior surface of the device housing. Circumferential antenna structures are described in co-assigned U.S. patent application Ser. No. 09/921,653, filed Aug. 3, 2001, CIRCUMFERENTIAL ANTENNA FOR AN IMPLANTABLE MEDICAL DEVICE, now issued as U.S. Pat. No. 6,456,256, and incorporated herein by reference in its entirety.

Near field module 220, in one embodiment, includes an inductively coupled transmitter/receiver 140A, as described relative to FIG. 1. Far field module 230, in one embodiment, includes RF receiver 120A, RF transmitter 110A and T/R switch 130A, as described relative to FIG. 1. In one embodiment, antenna 225 includes the structure described relative to antenna 150A of FIG. 1. In one embodiment, antenna 235 includes the structure described relative to antenna 101A of FIG. 1. In one embodiment, a switch is provided to select, and therefore communicate using, either near field module 220 or far field module 230.

According to one embodiment, far field communications conducted by far field module 230 are preferably conducted using an industrial, scientific, medical (ISM) band. One ISM band is between approximately 902 and 928 MHz, however frequencies above or below this figure are also possible. At another ISM band of frequencies, approximately 2.45 GHz, the effects of tissue absorption may undesirably attenuate the far field signal, and thus, limit the effective communication range. In some regions of the world, such as for example, Europe, frequencies near 868 to 870 MHz SRD (short range device) band may be available and thus, in one embodiment the implantable medical device and external device communicate at a frequency of 869.85 MHz. In one embodiment, the far field communication frequency is at the Medical Implant Communications Service (MICS) band, between approximately 402 and 405 MHz.

Medical module 240 is coupled to telemetry data bus 215 by interface 250. In one embodiment, interface 250 includes telemetry direct memory access (DMA) and data buffers. In the embodiment shown, interface 250 is coupled to system data bus 245. Bus 245 is further coupled to microprocessor 260, device random access memory (RAM) 270, device therapy circuit 280 and telemetry control circuit 290. In one embodiment, bus 245 includes a multiple conductor digital data bus. In one embodiment, microprocessor 260 includes the structure described relative to ΦP 102A and wakeup timer 180A of FIG. 1.

In various embodiments, microprocessor 260 includes a digital or analog processor adapted for managing data or signals on bus 245. Device RAM 270 provides storage for data or programming for execution by microprocessor 260. In one embodiment, device therapy circuit 280 includes a pulse generator or other therapeutic system. In one embodiment, therapy circuit 280 includes a monitoring circuit adapted for monitoring the condition or performance of an organ or other physiological parameter. In one embodiment, device therapy circuit 280 includes circuitry for monitoring the condition of implantable medical device 205. For example, in one embodiment, device therapy circuit 280 provides a signal based on remaining battery capacity to microprocessor 260. Telemetry control circuit 290 includes circuitry adapted for controlling telemetry functions relative to the modules coupled to telemetry data bus 215.

Figure 3:
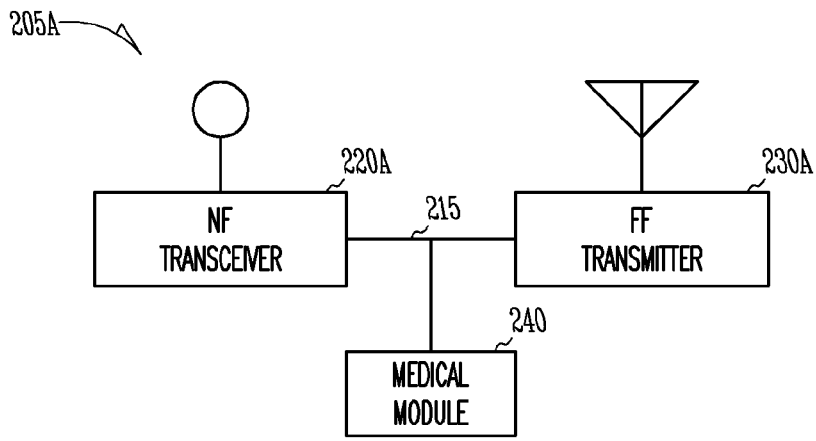
FIG. 3 is a block diagram of an embodiment of an implantable medical device having a near field transceiver and a far field transmitter.
Figure 4:
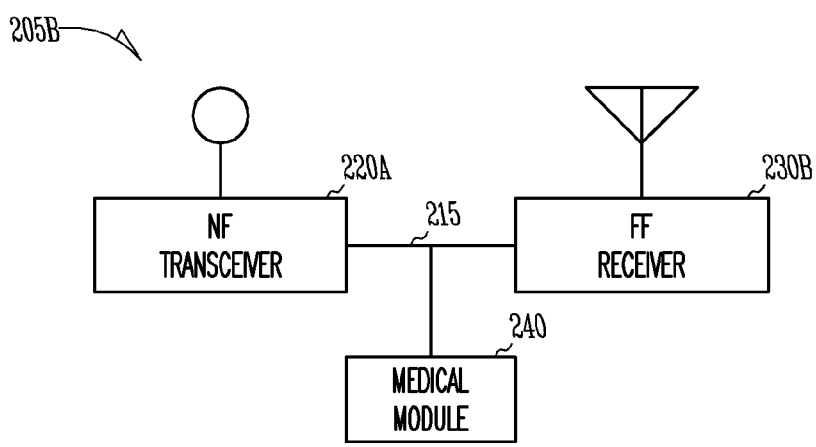
FIG. 4 is a block diagram of an embodiment of an implantable medical device having a near field transceiver and a far field receiver.
Figure 5:
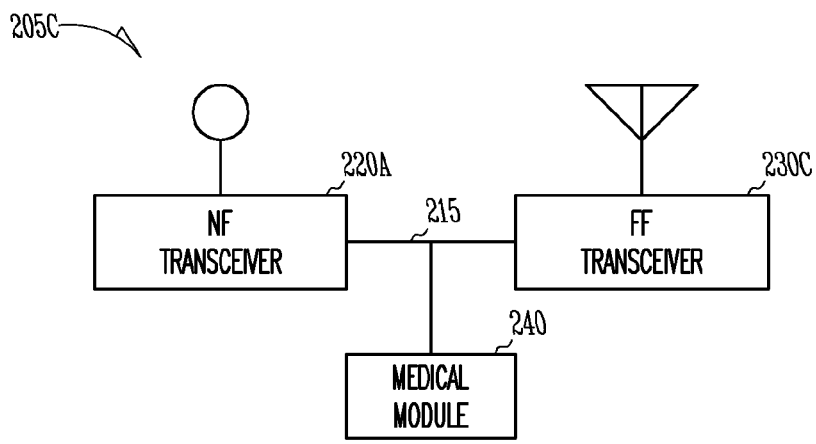
FIG. 5 is a block diagram of an embodiment of an implantable medical device having a near field transceiver and a far field transceiver.

FIGS. 3, 4 and 5 illustrate exemplary embodiments of implantable medical device 205, each of which includes a medical module 240 coupled to telemetry data bus 215 as previously described. For example, in FIG. 3, implantable medical device 205A is shown having near field transceiver 220A and far field transmitter 230A. In one embodiment, near field module 220 includes near field transceiver 220A. As a further example, FIG. 4 illustrates implantable medical device 205B having near field transceiver 220A and far field receiver 230B. In one embodiment, far field module 230 includes far field receiver 230B. As yet a further example, FIG. 5 illustrates implantable medical device 205C having near field transceiver 220A and far field transceiver 230C. In one embodiment, far field module 230 includes far field transceiver 230C. Other embodiments are also contemplated, such as, for example, a near field transmitter or receiver coupled to any of transmitter 230A, receiver 230B or transceiver 230C.

Consider next the operation of the present system. At the time of implantation, implantable medical device 205 may be programmed and controlled by a medical programmer, or external device, adapted to communicate using near field transceiver 220A. An embodiment of an external device is illustrated in FIG. 1. The programmer may include a flexible wand having a transceiver antenna that communicates with near field transceiver 220A. For example, in one embodiment, the programmer includes an inductive loop antenna and near field transceiver 220A also includes an inductive loop antenna. Following implantation of the device, subsequent programming and controlling may also be accomplished using near field transceiver 220A.

The embodiment illustrated in FIG. 3 allows implantable medical device 205A to transmit data using a far field transmission. For example, in one embodiment, the data includes operational conditions or parameters concerning implantable medical device 205A or the patient in which device 205A is implanted. In one embodiment, data is transmitted using far field transmitter 230A according to a schedule having a predetermined duty cycle or according to a programmed schedule. In one embodiment, data is transmitted using far field transmitter 230A upon the occurrence of a predetermined event or when a particular parametric value is exceeded. In one embodiment, data is transmitted using far field transmitter 230A in response to receiving a particular signal via near field transceiver 220A. In various embodiments, far field transmissions using transmitter 230A proceed until finished, for a predetermined period of time, or until a terminate signal is received via near field transceiver 220A.

The embodiment illustrated in FIG. 4 allows implantable medical device 205B to receive data using a far field transmission. For example, in one embodiment, the data includes programming information or parameters for implementation by implantable medical device 205B. The parameters may concern therapy for the patient in which implantable medical device 205B is implanted. In one embodiment, data is received using far field receiver 230B according to a schedule having a predetermined duty cycle or according to a programmed schedule. In one embodiment, data is received using far field receiver 230B upon the occurrence of a predetermined event or when a particular parametric value is exceeded. In one embodiment, data is received using far field receiver 230B in response to receiving a particular signal via near field transceiver 220A. In various embodiments, far field transmissions received using receiver 230B proceed until finished, for a predetermined period of time, or until a terminate signal is received via near field transceiver 220A or far field receiver 230B.

The embodiment illustrated in FIG. 5 allows implantable medical device 205C to both receive data and transmit data using a far field transmission. For example, in various embodiments, far field received or transmitted data includes programming information or parameters for implementation by implantable medical device 205C, concerning device 205C, or the patient in which device 205C is implanted. The parameters may concern therapy for the patient in which device 205C is implanted. In various embodiments, data is transmitted or received according to a schedule having a predetermined duty cycle or according to a programmed schedule. In one embodiment, data is received or transmitted using far field communication upon the occurrence of a predetermined event or when a particular parametric value is exceeded. In one embodiment, data is communicated using far field transceiver 230C in response to receiving a particular signal via near field transceiver 220A. In various embodiments, far field communications proceed until finished, for a predetermined period of time, or until a terminate signal is received via near field transceiver 220A or far field transceiver 230C. Far field transceiver 230C includes a far field transmitter and a far field receiver and in one embodiment, the far field transmitter communicates using a communication protocol that differs from that of the far field receiver.

In various embodiments, the communication modules enable one or more modes of communicating. The plurality of communication modes may each have full redundancy or each may provide different capabilities. For example, in one embodiment, a first communication mode supports receiving operational parameters and a second communication mode transmits diagnostic data.

Figure 6:
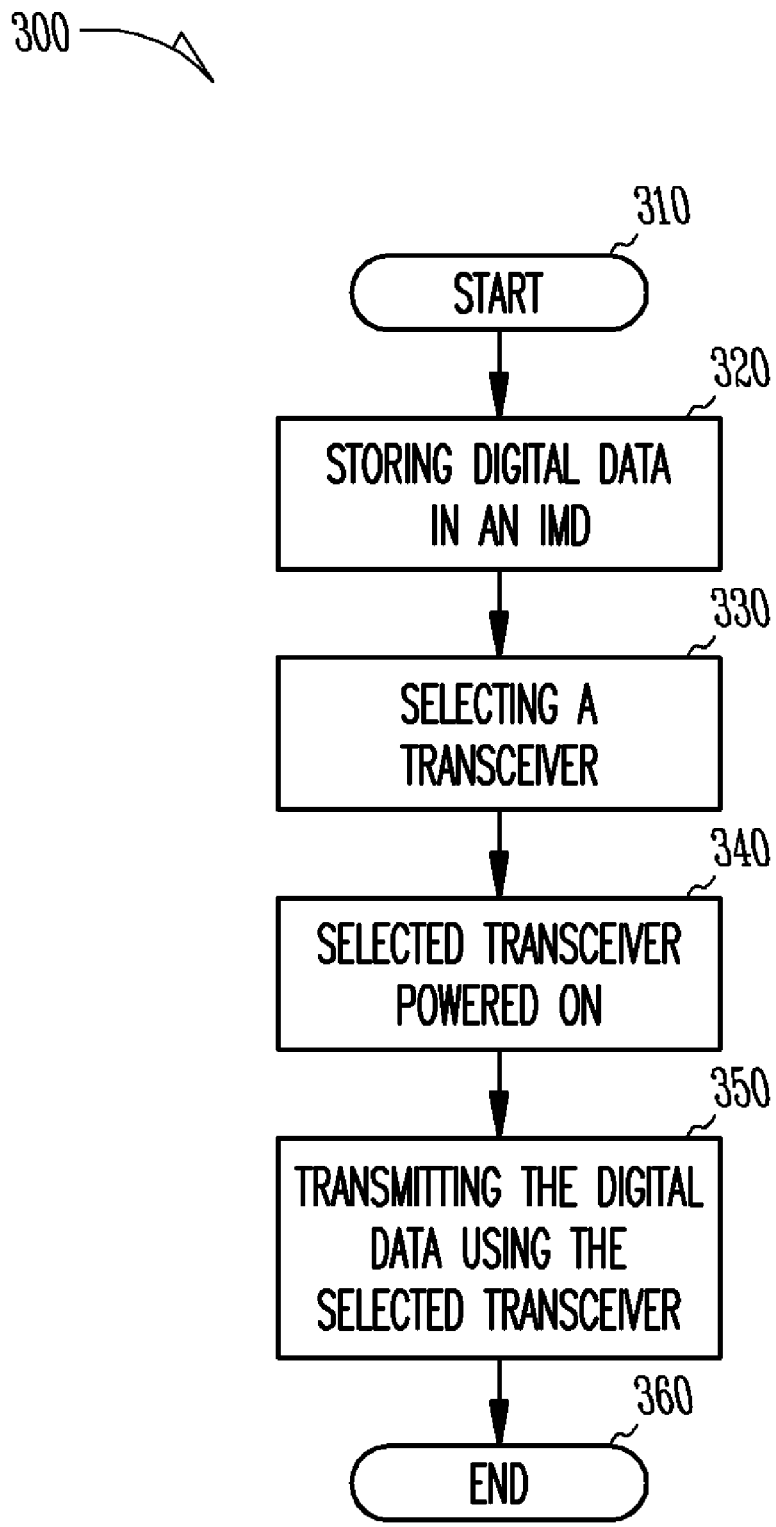
FIG. 6 is a flow chart illustrating a method of transmitting executed by an embodiment of the present subject matter.

FIG. 6 illustrates a method implemented by one embodiment of the present system. In the figure, method 300 concerns the transmission of data from an implantable medical device having a plurality of transmitters or transceivers. Beginning at 310, the method includes receiving or generating data at the implantable medical device, as noted at 320. For example, in one embodiment, data is received from electrodes or leads that terminate in various portions of the body and are coupled to the implantable medical device. In one embodiment, the data is processed by the implantable medical device and the results generated are stored and available for telemetering to a remote programmer. At 330, a transceiver is selected for transmitting the data to the remote programmer. In one embodiment, a transmitter is selected at 330.

The selected transmitter, or transceiver, may include a near field transmitter, a far field transmitter, or a combination of near and far field.

Continuing with the figure, at 340, the selected transceiver is powered on. In one embodiment, the process of turning on the selected transceiver includes entering an "awake" mode after departure from a "sleep" mode. At 350, an outbound signal, including the digital data previously stored, is wirelessly transmitted by the transmitter. The process ends at 360. The process may also be performed in an order which differs from that illustrated.

Figure 7:
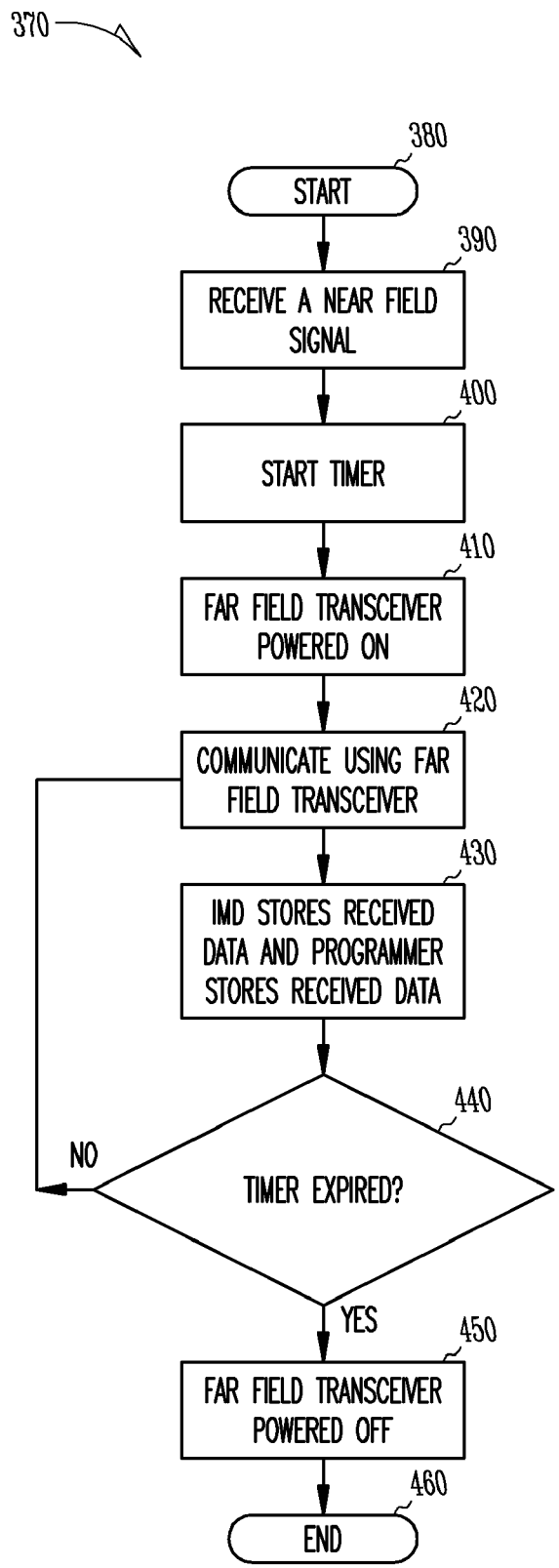
FIG. 7 is a flow chart illustrating a method of communicating executed by an embodiment of the present subject matter.

FIG. 7 illustrates method 370 which may be useful in programming or configuring an implantable medical device. Beginning at 380, a near field signal is received as illustrated at 390. In one embodiment, the near field signal marks the beginning of a time period, or window, during which the far field communication capabilities of the implantable medical device are available. In one embodiment, during predetermined times after the window, communications are conducted using the far field communication capabilities of the device. Upon receiving a signal using the near field link, the far field window remains open. The duration of the time period is monitored by a timer and at 400, the timer is started. At 410, following the start of the timer, the far field transceiver is powered on or otherwise enabled. At 420, wireless communications between the implantable medical device and the remote programmer are conducted using the far field transceiver. At 430, data encoded in the received signal is stored in memory coupled to the implantable medical device and outbound data is stored in memory accessible to the external programmer. In various embodiments, the data includes replacement programming or operating parameters that controls the operation of the implantable medical device. An inquiry as to the status of the timer occurs at 440 after which processing branches to 420 if the predetermined time period has not lapsed, or continues to 450 if the period has lapsed. At 450, the far field communication capabilities are terminated, and in one embodiment, this entails turning off power to the far field transceiver. The process ends at 460.

In one embodiment, the method illustrated in FIG. 7 includes checking for a terminate command in lieu of checking the timer for expiration. If a terminate command is received, either by the far field link or the near field link, then the far field transceiver is powered off. Otherwise, communications using the far field transceiver continues until receipt of a termination command. The termination command may save battery resources of the device by powering off the far field transceiver in advance of a signal from the timer.

Figure 8:
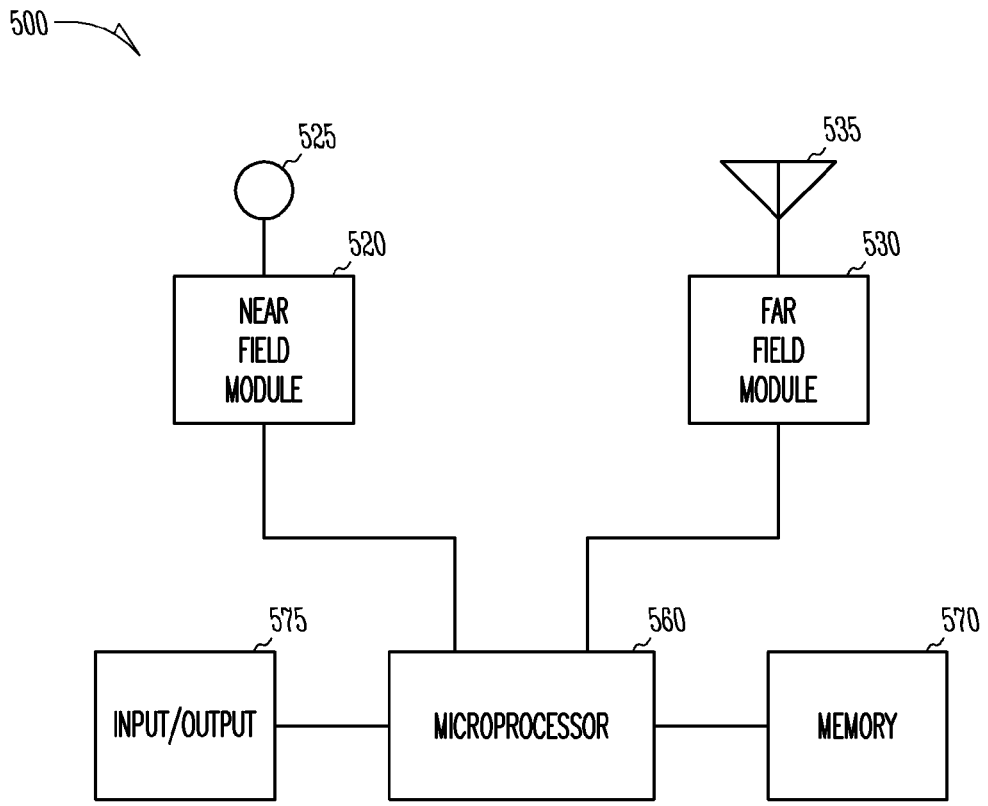
FIG. 8 is a block diagram of a programmer in accordance with the present subject matter.

FIG. 8 illustrates a programmer, or external device, in accordance with one embodiment of the present system. Programmer 500 includes near field module 520 and far field module 530, each coupled to microprocessor 560. Near field module 520 is coupled to antenna 525, here illustrated as a loop antenna suitable for inductive coupling. Far field module 530 is coupled to antenna 535, here illustrated as an antenna, and in various embodiments, includes a monopole or a dipole antenna. Microprocessor 560 is coupled to input/output module 575 and memory 570. In various embodiments, input/output module 575 includes a keyboard, bar code scanner, monitor, audio speaker, microphone, printer, storage media, wireless communication modules, or other device. In one embodiment, input/output module 575 provides an interface with which a human operator can communicate with an implantable medical device. Memory 570 provides storage for data and programming used by microprocessor 560. In one embodiment, memory 570 provides storage for data to be transmitted to, or received from, an implantable medical device.

In one embodiment, programmer 500 includes both a far field and near field communication module, as illustrated, with each module operating independent of the other. In one embodiment, programmer 500 includes either a far field communication module or a near field communication module.

Exemplary System

By way of example, and not by way of limitation, an exemplary system is described as follows.

In this embodiment, an inductive coupling provides a near field communication link. The inductive coupling is continuously available since it draws little or no power when receiving and is able to receive power from an external programmer for purposes of operating the implantable medical device. In addition, the inductive coupling is adapted to convey recharging power to the battery of the implantable medical device. In various embodiments, the near field communication link includes an optical link, an audible link, or an infrared link.

In one embodiment, the far field communication link draws power at a rate that is greater than that of the near field link. Also, in one embodiment, transmitting a far field signal draws a greater instantaneous current than does receiving a far field signal, however, the far field transmissions are of such short duration that receiving far field transmissions draws a greater total power. Consequently, far field reception is available according to a duty cycle. By way of example, the ability to receive a far field transmission exists for a short period of time each minute.

The ability to communicate using a plurality of modes, such as a far field and near field mode, may provide advantages that are not otherwise available with a single communication mode. For example, the availability of a second communication mode increases the likelihood that the programmer and implantable medical device can communicate reliably. In situations where one mode of communication is unavailable, it may be that another communications mode is available. In addition, whereas the far field communications means may operate according to a duty cycle, the near field communications link is continuously available, and therefore, available on demand. Furthermore, in some regions of the world, the ability to conduct far field communications may be restricted, and therefore, the availability of a near field link allows uninterrupted communications.

Using the far field communication link, one embodiment of the present system transmits a signal that may be translated as either "I'm OK" or "I'm not OK." In one embodiment, after receiving a "not OK" signal, the remote programmer commences a procedure whereby the patient, a doctor, or other responsible party, is contacted and, if warranted, the patient is invited to seek medical attention. Contacting the patient, doctor, or other responsible party may entail placing a telephone call, transmitting a pager message, sending an e-mail, broadcasting a radio message, or otherwise attempting to establish communications.

The present system also may find application in the operating room at the time of implantation of the medical device. For example, at the time of implantation, one embodiment allows using the far field link for initial configuration, diagnosis and set up procedures. Enhanced sterility, increased flexibility, and reduced burden are possible advantages achievable by reducing the reliance on the traditional programmer wand. Furthermore, one embodiment of the present system allows remote follow-up with the patient. This may reduce or eliminate the need for periodic visits to a clinic, thereby reducing system costs.

In one embodiment, security measures are implemented to assure that access to the implantable medical device is limited to authorized users. For example, in one embodiment, data transmitted from the implantable medical device is encrypted, or otherwise encoded, to restrict access. In one embodiment, encryption includes use of a key encryption system utilizing both a public key and a private key. In one embodiment, the implantable medical device is programmed to respond only to instructions from an authorized programmer. In one embodiment, the security system is implemented by means of a programming window of time that is triggered by an inductively coupled programmer wand.

In one embodiment, the near field link is continuously available and is used to "ping" the implantable medical device. The near field link is be used to establish communications and in a seamless transition, the far field link continues to communicate with the device after removal of the wand from the vicinity of the implantable medical device. For example, in one embodiment, a wand having an inductive coil is temporarily brought near the chest wall of the patient in a clinical setting, and upon removal of the wand from near the patient, communications continue using a far field link. At the conclusion of the session, marked by receipt of a signal received via the far field link, or upon a signal transmitted from the near field wand, the far field link is disabled. In one embodiment, the far field link is used to transmit new parameters or instruction code to the implantable medical device and the new parameters or code are triggered for implementation upon receipt of a command transmitted via the inductive coil or far field link.

Alternate Embodiments

Figure 9:
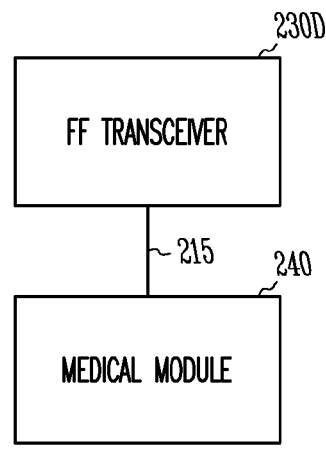
FIG. 9 is a block diagram of an embodiment of an implantable medical device having a far field transceiver.

In various embodiments, all telemetry with the implanted medical device is communicated using a far field transmitter, far field receiver, or a far field transceiver. FIG. 9 illustrates an embodiment of an implanted medical device having medical module 240 coupled to a far field transceiver 230D via telemetry data bus 215. The telemetry system, including far field transceiver 230D, of the implanted medical device is operated according to a duty cycle and the duty cycle is compatible with the operation of a suitable programmer. For example, the programmer may also be operated according to a complementary duty cycle or operated continuously.

In one embodiment, the medical device and the programmer communicate on a peer-to-peer basis and not on the basis of a master-slave relationship. For example, in one embodiment, the medical device and the programmer are cycled in phase according to a predetermined schedule. In this embodiment, the medical device and the programmer operate without establishing a master-slave relationship wherein one unit is superior to the other unit. By way of an example, in a system with a field communication link, the implanted medical device may attempt to receive data, or transmit data, without having first received an acknowledgment or ready signal from the programmer. In one embodiment, the implantable medical device and the programmer engage in a handshaking routine wherein each device has substantially equal autonomy.

The duty cycle of the implantable medical device may correspond to that of the programmer. For example, a 10% duty cycle of a medical device based on a 10 second period (that is, the device may transmit, or receive, a wireless signal for one second followed by nine seconds of dormancy) would be able to communicate with a programmer operated on a 10% duty cycle based on a 5 second period (that is, the programmer is active for one second followed by four seconds of dormancy). The medical device may also communicate with a programmer that is continuously active. In one embodiment, the communication link of the medical device is operated according to a duty cycle providing one second of activity followed by several seconds of dormancy.

In one embodiment, the duration of the window during which far field communications may be conducted, is dynamically adjustable. For example, after having established a communication link during the active period of a duty cycle, the programmer may instruct the medical device to maintain the far field communication link for a programmable period of time which differs from a duty cycle of the medical device. In this way, for example, the programmer can conduct uninterrupted communications with the medical device. In addition, the programmer may instruct the medical device to terminate the far field communication link at a predetermined time and without regard for the duty cycle.

In one embodiment, a near field link is used to mark the beginning of a session during which the far field communication link is available. The duration of the subsequent far field communication session may be determined by a duty cycle, fixed time period or an instruction or parameter received during the communication session. For example, in one embodiment, the far field communication link is available according to a predetermined duty cycle. Thus, the far field link is terminated upon the expiration of a predetermined window. As another example, the far field communication link may be available during the course of a medical procedure, such as, device implantation. In such an embodiment, the far field link may become available at the start of the procedure after first having been triggered by a near field communication link. The far field link may remain available for a predetermined duration, typically sufficient to allow completion of a particular medical procedure. In another example, the far field communication link is terminated upon receipt of a predetermined command or instruction received via the far field link or near field link. A terminate command may truncate the duty cycle that otherwise would determine the window duration.

In some regions of the world, or in certain locations, regulations may preclude the use of far field radio frequency transmissions. For example, in Japan, certain frequencies that are readily available in the United States of America are not available for far field RF transmissions. As another example, Federal Aviation Regulations enforced by the Federal Aviation Administration (FAA) prohibit the use of certain far field transmissions while airborne.

In such cases, these restrictions or regulations are satisfied by an embodiment of the present system having a configuration that does not transmit a far field RF signal unless it first receives a far field RF signal. In one embodiment, the near field link or far field link first receives a wake up signal before the far field transmitter is operated. In one embodiment, the implantable medical device receives and transmits using the same communication link. For example, if a far field signal is received, then a far field signal is transmitted. The far field signal may include an acknowledgment.

In one embodiment, the programmer is burdened with the task of arbitrating the communication links. The programmer is considered more robust since power may be derived from a metered line service or batteries that can be replaced without surgical procedures. In various embodiments, the external programmer is operated continuously or according to a duty cycle.

For example, the external programmer may be used with many different implantable medical devices, each having a unique identification code. The far field transmitter of the programmer may be operated continuously and the transmitted signal can be tailored to correspond with a particular implantable medical device by proper selection of the identification code. To establish a communication session with a particular implantable medical device, the programmer may continuously transmit a key and listen for a response. In this manner, the programmer need not know precisely the timing sequence and duty cycle of each individual implantable medical device. After the targeted implantable medical device wakes up and receives the far field transmission, the device transmit a far field acknowledgment signal.

In one embodiment, the duty cycle of the implantable medical device can be dynamically adjusted. For example, a low power consumption duty cycle may be operative during times when the implantable medical device is away from a medical facility, a medium power consumption duty cycle may be operative during times near a medical facility and a high power consumption duty cycle may be operative during a clinician visit at a medical facility. The level of power consumption may be associated with different duty cycles. For example, in one embodiment, the low power consumption duty cycle provides that the far field receiver is operated for one time period in 10,000 time periods whereas the far field receiver is operated continuously in the high power consumption duty cycle. In one embodiment, the particular duty cycle is selected based on receiving an external signal (near field or far field) or by an internal parameter detected by the implantable medical device.

In one embodiment, synchronization includes receiving a magnetic signal. The magnetic signal may be received from a wand coupled to a programmer. The signal may correspond to an edge or transition of a magnetic field strength or magnetic alignment. In one embodiment, the implantable medical device responds to a minimum magnetic field strength.

CONCLUSION

Other embodiments of the present system are also contemplated. For example, in one embodiment, the implantable medical device, or programmer, has more than two transmitters, transceivers, or receivers. In one embodiment, an implantable medical device is adapted to include a single transceiver having a plurality of operational modes wherein one mode includes transmitting, or receiving, a substantial signal at a near field strength and a second mode includes transmitting, or receiving, a substantial signal at a far field strength.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable medical device (IMD) comprising:
   a far field RF transmitter and receiver;
   a controller circuit communicatively coupled to the RF transmitter and receiver; and
   a wakeup timer circuit integral to, or communicatively coupled to, the controller,
   wherein the controller circuit is configured to:
      initiate power up of the RF transmitter and receiver during a wakeup interval defined by the wakeup timer circuit;
      detect a digital key received from a second device during the wakeup interval;
      transmit a response using the RF transmitter when the digital key is received; and
      receive a communication from the second device and resynchronize the wake-up timer according to a time of the communication.

2. The IMD of claim 1, wherein the controller circuit is configured to:
   calculate an average of the amount the wakeup timer circuit is adjusted for resynchronization; and
   adjust the wakeup timer circuit using the calculated average.

3. The IMD of claim 1, wherein the controller circuit is configured to:
   determine an amount of time since the previous communication with the second device; and
   adjust the wakeup timer circuit using the determined time.

4. The IMD of claim 1, wherein the controller circuit is configured to resynchronize the wakeup timer circuit by aligning the wakeup interval to the start of the communication.

5. The IMD of claim 1, wherein the controller circuit is configured to resynchronize the wakeup timer circuit by setting the wakeup timer ahead or behind the start of the communication.

6. The IMD of claim 1, wherein the wakeup interval timed by the wakeup circuit is different from the wakeup interval of the second device.

7. The IMD of claim 6, wherein the wakeup interval is long enough to receive a plurality of digital keys.

8. The IMD of claim 1, wherein the controller circuit is configured to:
   detect a different digital key received from a second device during the wakeup interval; and
   resynchronize the wake-up timer according to a time the different digital key was received.

9. The IMD of claim 1, wherein the controller circuit is configured to change the wakeup interval according to the communication from the second device.

10. The IMD of claim 1, wherein the controller circuit is configured to shorten the wakeup interval when a low battery condition is detected.

11. The IMD of claim 1, wherein the controller circuit is configured to initiate transmitting data in the response before receiving a message indicating that the second device is ready.

12. The IMD of claim 1, wherein the controller circuit is configured to receive data from the second device without receiving an acknowledge of the response.

13. The IMD of claim 1, wherein, upon detection of a specified event, the controller circuit is configured to communicate as a master device according to a specified master/slave communication protocol during the wakeup interval.

14. The IMD of claim 13, wherein the controller circuit is configured to:
   transmit a digital key to the second device;
   establish a communications session with the second device when a response to the digital key is received from the second device; and
   initiate transmission of a terminate command to end the communications session.

15. The IMD of claim 1, wherein the controller circuit is configured to enable the far field transmitter and receiver for an interval of time indicated in the communication from the second device.

16. A method comprising:
supplying power to a far field RF transmitter and receiver of an IMD according to a wakeup interval determined by a device wakeup timer;
detecting a digital key received from a second device during the wakeup interval;
transmitting a response using the RF transmitter when the digital key is received;
receiving a communication from the second device; and
re-synchronizing the device wake-up timer according to a time of the communication.

17. The method of claim 16, wherein re-synchronizing the device wake-up timer includes aligning the wakeup interval to the start of the communication.

18. The method of claim 16, wherein re-synchronizing the device wake-up timer includes setting the wakeup timer ahead or behind the start of the communication.

19. The method of claim 16, including communicating with the IMD as a master device according to a specified master/slave communication protocol during the wakeup interval upon an IMD detection of a specified event.

20. The method of claim 19, wherein communicating with the IMD as a master device includes:
initiating communications with the second device;
establishing a communications session with the second device when a response is received from the second device; and
transmitting a terminate command to end the communications session.

* * * * *